United States Patent [19]
Bandman et al.

[11] Patent Number: 5,985,635
[45] Date of Patent: Nov. 16, 1999

[54] NUCLEIC ACIDS ENCODING NOVEL HUMAN SERINE/THREONINE PROTEIN KINASES

[75] Inventors: Olga Bandman, Mountain View; Surya K. Goli, Sunnyvale; Jennifer L. Hillman, San Jose, all of Calif.

[73] Assignee: Incyte Pharmaceuticals, Inc., Palo Alto, Calif.

[21] Appl. No.: 08/749,902

[22] Filed: Nov. 15, 1996

[51] Int. Cl.$^6$ .............................. C12N 15/54; C12N 9/12
[52] U.S. Cl. .................. 435/194; 435/69.1; 435/252.3; 435/254.11; 435/320.1; 435/325; 536/23.2; 536/24.31
[58] Field of Search ................................. 435/69.1, 325, 435/254.11, 252.3, 194, 320.1; 536/23.2, 24.31

[56] References Cited

PUBLICATIONS

Wang et al., Proc. Natl. Acad. Sci, 92, 3933–3937, Apr. 1995.
*The Protein Kinase Facts Book,* Hardie, G., et al., pp. 58–63 ("cAMP–dependent protein kinase (vertebrates)") (1995).
*Harrison's Principles of Internal Medicine,* Isselbacher, K.J., et al., 1:416–431 (1994).
*Harrison's Principles of Internal Medicine,* Isselbacher, K.J., et al., 2:1887 (1994).
Egan, S.E., et al., "The pathway to signal achievement" *Nature,* 365:781–783 (1993).
Hershey, J.W.B., "Protein Phosphorylation Controls Translation Rates" *J. Biol. Chem.,* 264:20823–20826 (1989).
Grove, J.R., et al., "Cloning and Expression of Two Human p70 S6 Kinase Polypeptides Differing Only at Their Amino Termini" *Mol. Cell. Biol.,* 11:5541–5550 (1991).
Harmann, B., et al., "cDNA encoding a 59 kDa homolog of ribosomal protein S6 kinase from rabbit liver" *FEBS Letters,* 273:248–252 (1990).
Nezu, J., (GI 1480861), GenBank Sequence Database (Accession 1480861), National Center for Biotechnology Information, National Library of Medicine, Bethesda, Maryland 20894.
Su, J.Y., et al., "Cloning and Characterization of a Novel Serine/Threonine Protein Kinase Expressed in Early Xenopus Embryos" *Am. Soc. Biochem. Mol. Biol.,* 271:14430–14437 (1996).
Ayala et al., Modern Genetics, pp. 45–48, 1980, Benjamin/Cummings Publishing Company, Inc.
Sambrook et al., Molecular Cloning, A Laboratory Manual, Second Edition, 16.2–16.30 and 17.3–17.28, 1989, Cold Spring Harbor Laboratory Press,.

*Primary Examiner*—Sally P. Teng
*Attorney, Agent, or Firm*—Incyte Pharmaceuticals, Inc.

[57] ABSTRACT

The present invention provides human serine/threonine kinase (HSTK) and polynucleotides which identify and encode HSTK. The invention also provides genetically engineered expression vectors and host cells comprising the nucleic acid sequences encoding HSTK and a method for producing HSTK. The invention also provides for use of HSTK and agonists, antibodies, or antagonists specifically binding HSTK, in the prevention and treatment of diseases associated with expression of HSTK. Additionally, the invention provides for the use of antisense molecules to polynucleotides encoding HSTK for the treatment of diseases associated with the expression of HSTK. The invention also provides diagnostic assays which utilize the polynucleotide, or fragments or the complement thereof, and antibodies specifically binding HSTK.

6 Claims, 12 Drawing Sheets

```
                9              18              27              36              45              54
5' CTT TGT AAA ATT TTG GAG AAG GGA AGT NGG AAC ACA AGG AAG GAC CGC TCA CCC 63              72              81              90              99             108
   GCG GAC TCA GGG CTG GCG GCG GGA CTC CAG GAC CCT GGG TCC AGC ATG GAG GTG
                                                                   M   E   V 117             126             135             144             153             162
   GTG GAC CCG CAG CAG CTG GGC ATG TTC ACG GAG GGC GAG CTG ATG TCG GTG GGT
   V   D   P   Q   Q   L   G   M   F   T   E   G   E   L   M   S   V   G 171             180             189             198             207             216
   ATG GAC ACG TTC ATC CAC CGN ATC GAC TCC ACC GAG GTC ATC TAC CAG CCG CGC
   M   D   T   F   I   H   R   I   D   S   T   E   V   I   Y   Q   P   R 225             234             243             252             261             270
   CGC AAG CGG GCC AAG CTC ATC GGC AAG TAC CTG ATG GGG GAC CTG CTG GGG GAA
   R   K   R   A   K   L   I   G   K   Y   L   M   G   D   L   L   G   E 279             288             297             306             315             324
   GGC TCT TAC GGC AAG GTG AAG GAG GTG CTG GAC TCG GAG ACG CTG TGC AGG AGG
   G   S   Y   G   K   V   K   E   V   L   D   S   E   T   L   C   R   R 333             342             351             360             369             378
   GCC GTC AAG ATC CTC AAG AAG AAG AAG TTG CGA AGG ATC CCC AAC GGG GAG GCC
   A   V   K   I   L   K   K   K   K   L   R   R   I   P   N   G   E   A 387             396             405             414             423             432
   AAC GTG AAG AAG GAA ATT CAA CTA CTG AGG AGG TTA CGG CAC AAA AAT GTC ATC
   N   V   K   K   E   I   Q   L   L   R   R   L   R   H   K   N   V   I 441             450             459             468             477             486
   CAG CTG GTG GAT GTG TTA TAC AAC GAA GAG AAG CAG AAA ATG TAT ATG GTG ATG
   Q   L   V   D   V   L   Y   N   E   E   K   Q   K   M   Y   M   V   M 495             504             513             522             531             540
   GAG TAC TGC GTG TGT GGC ATG CAG GAA ATG CTG GAC AGC GTG CCG GAG AAG CGT
   E   Y   C   V   C   G   M   Q   E   M   L   D   S   V   P   E   K   R 549             558             567             576             585             594
   TTC CCA GTG TGC CAG GCC CAC GGG TAC TTC TGT CAG CTG ATT GAC GGC NTG GGG
   F   P   V   C   Q   A   H   G   Y   F   C   Q   L   I   D   G   X   G 603             612             621             630             639             648
   TAC CTG CAT NGC CAG GGN ATT GTG CAC AAG GGC ATC AAG CCG GGG AAC CTG CTG
   Y   L   H   X   Q   G   I   V   H   K   G   I   K   P   G   N   L   L 657             666             675             684             693             702
   CTC ACC ACC GGT GGC ACC CTC AAA ATC TCC GAC CTG GGC GTG GCC GAG GCA CTG
   L   T   T   G   G   T   L   K   I   S   D   L   G   V   A   E   A   L 711             720             729             738             747             756
   CAC CCG TTC GCN GCG GAC GAC ACC TGC CGG ACC AGC CAG GGC TCC CCG GCT TTC
   H   P   F   A   A   D   D   T   C   R   T   S   Q   G   S   P   A   F
```

FIGURE 1A

```
        765            774            783            792            801            810
CAG CCG CCC GAN ATT GCC AAC GGC CTG GAC ACC TTC TCC GGC TTC AAG GTG GAC
 Q   P   P   X   I   A   N   G   L   D   T   F   S   G   F   K   V   D 819            828            837            846            855            864
ATC TGG TCG GCT GGG GTC ACC CTC TAC AAC ATC ACC ACG GGT CTG TAC CCC TTC
 I   W   S   A   G   V   T   L   Y   N   I   T   T   G   L   Y   P   F 873            882            891            900            909            918
GAA GGG GAC AAC ATC TAC AAG TTG TTT GAG AAC ATC GGG AAG GGG AGC TAC GCC
 E   G   D   N   I   Y   K   L   F   E   N   I   G   K   G   S   Y   A 927            936            945            954            963            972
ATC CCG GGC GAC TGT GGC CCC CCG CTC TCT GAC CTG CTG AAA GGG ATG CTT GAG
 I   P   G   D   C   G   P   P   L   S   D   L   L   K   G   M   L   E 981            990            999           1008           1017           1026
TAC GAA CCG GCC AAG AGG TTC TCC ATC CGG CAG ATC CGG CAG CAC AGC TGG TTC
 Y   E   P   A   K   R   F   S   I   R   Q   I   R   Q   H   S   W   F 1035           1044           1053           1062           1071           1080
CGG AAG AAA CAT CCT CCG GCT GAA GCA CCA GTG CCC ATC CCA CCG AGC CCA GAC
 R   K   K   H   P   P   A   E   A   P   V   P   I   P   P   S   P   D 1089           1098           1107           1116           1125           1134
ACC AAG GAC CGG TGG CGC AGA TGG ACT GTG GTG CCG TAC TTG GAG GAC CTG CAC
 T   K   D   R   W   R   R   W   T   V   V   P   Y   L   E   D   L   H 1143           1152           1161           1170           1179           1188
GGC GCG GAC GAG GAC GAG GAC CTC TTC GAC ATC GAG GAT GAC ATC ATC TAC ACT
 G   A   D   E   D   E   D   L   F   D   I   E   D   D   I   I   Y   T 1197           1206           1215           1224           1233           1242
CAG GAC TTC ACG GTG CCC GGA CAG GTC CCA GAA GAG GAG GCC AGT CAC AAT GGA
 Q   D   F   T   V   P   G   Q   V   P   E   E   E   A   S   H   N   G 1251           1260           1269           1278           1287           1296
CAG CGC CGG GGC CTC CCC AAG GCC GTG TGT ATG AAC GGC ACA GAG GCG GGC GCA
 Q   R   R   G   L   P   K   A   V   C   M   N   G   T   E   A   G   A 1305           1314           1323           1332           1341           1350
GTG AGC ACC AAA TCC AGG GCG GAG GGC CGG GCC CCC AAC CCT GCC CGC AAG GCC
 V   S   T   K   S   R   A   E   G   R   A   P   N   P   A   R   K   A 1359           1368           1377           1386           1395           1404
TGC TCC GCC AGC AGC AAG ATC CGC CGG CTG TNG GCC TGC AAG CAG CAG TGA GGC
 C   S   A   S   S   K   I   R   R   L   X   A   C   K   Q   Q 1413           1422           1431           1440           1449           1458
TGG CCG CCT GCA GCC CGT GTC CAG GAN CNC CGC CAG GTG NCG CNC CAG GCC CTC

AGT CTT CC 3'
```

FIGURE 1B

```
                 9              18              27              36              45              54
5' NNG TAT CNC TGC CAN GGN GGC CCC CAC CCN AAA NCA GGG GGG TNG GGG CCG GCC 63              72              81              90              99             108
    GGC CAG GGC CAT GTC CTG AGN CCC CNN GGC GTG CCT CCT GGA ACA GAT ATG CCC
                                                                        M   P 117             126             135             144             153             162
    GCC AGC CAG CCC ATT GAC NTC CCG GGC GCC AAG AAN AGG GGC AAG AAN AAT AAG
     A   S   Q   P   I   D   X   P   G   A   K   X   R   G   K   X   N   K 171             180             189             198             207             216
    CGC GGC CGG GCC ACC GAC AGC TTC TCG GGC AGG TTT GAA NAC GTC TAC CAN CTG
     R   G   R   A   T   D   S   F   S   G   R   F   E   X   V   Y   X   L 225             234             243             252             261             270
    CAG GAA NAT NTG CTG GGG GAG GGC GCT CAT GCC CGA GTG CAG ACC TGC ATT AAC
     Q   E   X   X   L   G   E   G   A   H   A   R   V   Q   T   C   I   N 279             288             297             306             315             324
    CTG ATC ACC AGC CAG GAG TAC NCC GTC AAN ATC ATT GNT TTT TTT NCA GGC CAC
     L   I   T   S   Q   E   Y   X   V   X   I   I   X   F   F   X   G   H 333             342             351             360             369             378
    ATT CGG AGC AGG GTT TTC AGG GAG GTG GAG ATG CTG TAC CAG TGC CAG GGA CAC
     I   R   S   R   V   F   R   E   V   E   M   L   Y   Q   C   Q   G   H 387             396             405             414             423             432
    AGG AAC GTC CTA GAG CTG ATT GAG TTC TTC GAG GAG GAG GAC CGC TTC TAC CTG
     R   N   V   L   E   L   I   E   F   F   E   E   E   D   R   F   Y   L 441             450             459             468             477             486
    GTG TTT GAG AAG ATG CGG GGA GGC TCC ATC CTG AGC CAC ATC CAC AAG CGC CGG
     V   F   E   K   M   R   G   G   S   I   L   S   H   I   H   K   R   R 495             504             513             522             531             540
    CAC TTC AAC GAG CTG GAG GCC AGC GTG GTG GTG CAG GAC GTG GCC AGC GCC TTG
     H   F   N   E   L   E   A   S   V   V   V   Q   D   V   A   S   A   L 549             558             567             576             585             594
    GAC TTT CTG CAT AAC AAA GGC ATC GCC CAC AGG GAC CTA AAG CCG GAA AAC ATC
     D   F   L   H   N   K   G   I   A   H   R   D   L   K   P   E   N   I 603             612             621             630             639             648
    CTC TGT GAG CAC CCC AAC CAG GTC TCC CCC GTG AAG ATC TGT GAC TTC GAC CTG
     L   C   E   H   P   N   Q   V   S   P   V   K   I   C   D   F   D   L 657             666             675             684             693             702
    GGC AGC GGC ATC AAA CTC AAC GGG GAC TGC TCC CCT ATC TCC ACC CCG GAG CTG
     G   S   G   I   K   L   N   G   D   C   S   P   I   S   T   P   E   L
```

FIGURE 2A

```
         711            720            729            738            747            756
CTC ACT CCG TGC GGC TCG GCG GAG TAC ATG GCC CCG GAG GTA GTG GAG GCC TTC
 L   T   P   C   G   S   A   E   Y   M   A   P   E   V   V   E   A   F 765            774            783            792            801            810
AGC GAG GAG GCT AGC ATC TAC GAC AAG CGC TGC GAC CTG TGG AGC CTG GGC GTC
 S   E   E   A   S   I   Y   D   K   R   C   D   L   W   S   L   G   V 819            828            837            846            855            864
ATC TTG TAT ATC CTA CTC AGC GGC TAC CCG CCC TTC GTG GGC CGC TGG TGG CAG
 I   L   Y   I   L   L   S   G   Y   P   P   F   V   G   R   W   W   Q 873            882            891            900            909            918
CGA CTG CGG CTG GGA CCG CTG ATG TAC GAC ATG CTC ACT GGA TCG CCG CCC TTT
 R   L   R   L   G   P   L   M   Y   D   M   L   T   G   S   P   P   F 927            936            945            954            963            972
ACC GCA GAG AAC CGG AAG AAA ACC ATG GAT AAG ATC ATC AGG GGC AAG CTG GCA
 T   A   E   N   R   K   K   T   M   D   K   I   I   R   G   K   L   A 981            990            999           1008           1017           1026
CTN CCC CCC TAC CTC ACC CCA GAT GCC CGG GAC CTT GTC AAA AAG TTT CTG AAA
 L   P   P   Y   L   T   P   D   A   R   D   L   V   K   K   F   L   K 1035           1044           1053           1062           1071           1080
CGG AAT CCC AGC CAG CGG ATT GGG GGT GGC CCA GGG GAT GCT GCT GAT GTG CAG
 R   N   P   S   Q   R   I   G   G   G   P   G   D   A   A   D   V   Q 1089           1098           1107           1116           1125           1134
AGA CAT CCC TTT TTC CGG CAC ATG AAT TGG GAC GAC CTT CTG GCC TGG CGT GTG
 R   H   P   F   F   R   H   M   N   W   D   D   L   L   A   W   R   V 1143           1152           1161           1170           1179           1188
GAC CCC CCT TTC AGG CCC TGT CTG CAG TCA GAG GAG GAC GTG AGC CAG TTT GAT
 D   P   P   F   R   P   C   L   Q   S   E   E   D   V   S   Q   F   D 1197           1206           1215           1224           1233           1242
ACC CGC TTC ACA CGG CAG ACG CCG GTG GAC AGT CCT GAT GAC ACA GCC CTC AGC
 T   R   F   T   R   Q   T   P   V   D   S   P   D   D   T   A   L   S 1251           1260           1269           1278           1287           1296
GAG AGT GCC AAC CAG GCC TTC CTG GGC TTC ACA TAC GTG GCG CCG TCT GTC CTG
 E   S   A   N   Q   A   F   L   G   F   T   Y   V   A   P   S   V   L 1305           1314           1323           1332           1341           1350
GAC AGC ATC AAG GAG GGC TTC TCC TTC CAG CCC AAG CTG CGC TCA CCC AGG CGC
 D   S   I   K   E   G   F   S   F   Q   P   K   L   R   S   P   R   R
```

FIGURE 2B

```
       1359           1368           1377           1386           1395           1404
CTC AAC AGT AGC CCC CGG GTC CCC GTC AGC CCC CTC AAG TTC TCC CCT TTT GAG
 L   N   S   S   P   R   V   P   V   S   P   L   K   F   S   P   F   E 1413           1422           1431           1440           1449           1458
GGG TTT CGG CCC AGC CCC AGC CTG CCG GAG CCC ACG GAG CTA CCT CTA CCT CCA
 G   F   R   P   S   P   S   L   P   E   P   T   E   L   P   L   P   P 1467           1476           1485           1494           1503           1512
CTC CTG CCA CCG CCG CCG CCC TCG ACC ACC GCC CCT CTC CCC ATC CGT CCC CCC
 L   L   P   P   P   P   P   S   T   T   A   P   L   P   I   R   P   P 1521           1530           1539           1548           1557           1566
TCA GGG ACC AAG AAG TCC AAG AGG GGC CGT GGG CGT CCA GGG CGT AGG AAG CCG
 S   G   T   K   K   S   K   R   G   R   G   R   P   G   R   R   K   P 1575           1584           1593           1602
GGT GGG GGT GAG GGT AGC CCT TGA GCC CTG TCC CTG CGG CTG T 3'
 G   G   G   E   G   S   P
```

FIGURE 2C

```
  1   M - - - - - - E V V D P Q Q L G M F T E G E L M S V G M D T    HSTK-1
  1   M - - - - - - E V V D P Q Q L G M F T E G E L M S V G M D T    G1480861
  1   M L C P S S M D E E G S E E I G F L G D - - - L S V G M D T    g1016651

25   F I H R I D S T E V I Y Q P R R K R A K L I G K Y L M G D L    HSTK-1
 25   F I H R I D S T E V I Y Q P R R K R A K L I G K Y L M G D L    G1480861
 28   F I H R I D S T E V I Y Q P R R K R A K L V G K Y L M G D L    g1016651

55   L G E G S Y G K V K E V L D S E T L C R R A V K I L K K K K    HSTK-1
 55   L G E G S Y G K V K E V L D S E T L C R R A V K I L K K K K    G1480861
 58   L G E G S Y G K V K E M L D S D T L C R R A V K I L K K K K    g1016651

85   L R R I P N G E A N V K K E I Q L L R R L R H K N V I Q L V    HSTK-1
 85   L R R I P N G E A N V K K E I Q L L R R L R H K N V I Q L V    G1480861
 88   L R R I P N G E A N V K K E I Q L L R R L R H R N V I Q L V    g1016651

115   D V L Y N E E K Q K M Y M V M E Y C V G M Q E M L D S V P      HSTK-1
115   D V L Y N E E K Q K M Y M V M E Y C V G M Q E M L D S V P      G1480861
118   D V L Y N E E K Q K M Y M V M E Y C V G M Q E M L D S V Q      g1016651

145   E K R F P V C Q A H G Y F C Q L I D G X G Y L H X Q G I V H    HSTK-1
145   E K R F P V C Q A H G Y F C Q L I D G L E Y L H S Q G I V H    G1480861
148   D K H F P V F Q A H G Y F C Q L I D G L E Y L H S Q G I V H    g1016651

175   K G I K P G N L L L T T G G T L K I S D L G V A E A L H P F    HSTK-1
175   K D I K P G N L L L T T G G T L K I S D L G V A E A L H P F    G1480861
178   K D I K P G N L L L T T D G T L K I S D L G V A E A L H P F    g1016651

205   A A D D T C R T S Q G S P A F Q P P X I A N G L D T F S G F    HSTK-1
205   A A D D T C R T S Q G S P A F Q P P E I A N G L D T F S G F    G1480861
208   A E G D T C R T S Q G S P A F Q P P E I A N G L D T F S G F    g1016651

235   K V D I W S A G V T L Y N I T T G L Y P F E G D N I Y K L F    HSTK-1
235   K V D I W S A G V T L Y N I T T G L Y P F E G D N I Y K L F    G1480861
238   K V D I W S A G V T L Y N I T T G L Y P F E G D N I Y K L F    g1016651

265   E N I G K G S Y A I P G D C G P P L S D L L K G M L E Y E P    HSTK-1
265   E N I G K G S Y A I P G D C G P P L S D L L K G M L E Y E P    G1480861
268   E N I G K G D Y S I P E E C G P L L S D L L R G M L E Y D P    g1016651

295   A K R F S I R Q I R Q H S W F R K K H P P A E A P V P I P P    HSTK-1
295   A K R F S I R Q I R Q H S W F R K K H P P A E A P V P I P P    G1480861
298   A K R F S I Q Q I R Q H N W F R K K H P H M D P I V P I P P    g1016651

325   S P D T K D R W R R W T V V P Y L E D L H G A D E D E D L F    HSTK-1
325   S P D T K D R W R S M T V V P Y L E D L H G A D E D E D L F    G1480861
328   S P E T K D R W R S L T V V P Y L E D L H G Y S E E E D L C    g1016651

355   D I E D D I I Y T Q D F T V P G Q V P E E E A S H N G Q R R    HSTK-1
355   D I E D D I I Y T Q D F T V P G Q V P E E E A S H N G Q R R    G1480861
358   D F E D D I I Y T Q D F T V P G Q V A E D D Y F A Q T Q S T    g1016651

385   G L P K A V C M N G T E A G A V S T K S R A E G R A P N P A    HSTK-1
385   G L P K A V C M N G T E A A Q L S T K S R A E G R A P N P A    G1480861
388   A P S K Q L C M N G T E S - Q L K T E R R V - - - S S S Q      g1016651

415   R K A C S A S S K I R R L X A C K Q Q                          HSTK-1
415   R K A C S A S S K I R R L S A C K Q Q                          G1480861
414   R K A S T T G S K V R K L S A C K Q Q                          g1016651
```

```
301  D L V K K F L K R N P S Q R I G G P G D A A D V Q R H P F F R H M N W D D L L    HSTK-2
322  D L L K K L L K R N A A S R L G A G P G D A G E V Q A H P F F R H I N W E E L L    g189508
322  D L L K K L L K R N A A S R L G A G P G D A G E V Q A H P F F R H I N W E E L L    g1562.

341  A W R V D P P F R P C L Q S E E D V S Q F D T R F T R Q T P V D S P D D T A L S    HSTK-2
362  A R K V E P P F K P L L Q S E E D V S Q F D S K F T R Q T P V D S P D D S T L S    g189508
362  A R K V E P P F K P L L Q S E E D V S Q F D S K F T R Q T P V D S P D D S T L S    g1562.

381  E S A N Q A F L G F T Y V A P S V L D S I K E G F S F Q P K L R S P R R L N S S    HSTK-2
402  E S A N Q V F L G F T Y V A P S V L E S V K E K F S F E E P K I R S P R R F I G S    g189508
402  E S A N Q V F L G F T Y V A P S V L E S V K E K F S F E E P K I R S P R R F I G S    g1562.

421  P R V P V S P L K F S P F E G F R - - - - - P S P S L P E P T E L P L P P - -    HSTK-2
442  P R T P V S P V K F S P - G D F W G R G A S A S T A N P Q T P V E Y P M E T S G    g189508
442  P R T P V S P V K F S P - G D F W G R G A S A S T A N P Q T P V E Y P M E T S G    g1562.

453  - - L L P P P P S T T A P L P I R P P S G T K K S K R G R G R P G R R K P G    HSTK-2
481  I E Q M D V T M S G E A S A P L P I R Q P N S G P Y K K Q A F P M I S K R - P E    g189508
481  I E Q M D V T T S G E A S A P L P I R Q P N S G P Y K K Q A F P M I S K R - P E    g1562.

490  G G E G S P    HSTK-2
520  H L R M N L    g189508
520  H L R M N L    g1562.
```

FIGURE 4B

NUCLEIC ACIDS ENCODING NOVEL HUMAN SERINE/THREONINE PROTEIN KINASES

FIELD OF THE INVENTION

This invention relates to nucleic acid and amino acid sequences of a novel serine/threonine protein kinases and to the use of these sequences in the diagnosis, prevention, and treatment of cancer, inflammatory diseases, and disorders that affect growth and development.

BACKGROUND OF THE INVENTION

Kinases regulate many different cell proliferation, differentiation, and signaling processes by adding phosphate groups to proteins. Uncontrolled signaling has been implicated in a variety of disease conditions including inflammation, cancer, arteriosclerosis, and psoriasis. Reversible protein phosphorylation is the main strategy for controlling activities of eukaryotic cells. It is estimated that more than 1000 of the 10,000 proteins active in a typical mammalian cell are phosphorylated. The high energy phosphate which drives activation is generally transferred from adenosine triphosphate molecules (ATP) to a particular protein by protein kinases and removed from that protein by protein phosphatases.

Phosphorylation occurs in response to extracellular signals (hormones, neurotransmitters, growth and differentiation factors, etc), cell cycle checkpoints, and environmental or nutritional stresses and is roughly analogous to turning on a molecular switch. When the switch goes on, the appropriate protein kinase activates a metabolic enzyme, regulatory protein, receptor, cytoskeletal protein, ion channel or pump, or transcription factor.

The kinases comprise the largest known protein group, a superfamily of enzymes with widely varied functions and specificities. They are usually named after their substrate, their regulatory molecules, or some aspect of a mutant phenotype. With regard to substrates, the protein kinases may be roughly divided into two groups; those that phosphorylate tyrosine residues (protein tyrosine kinases, PTK) and those that phosphorylate serine or threonine residues (serine/threonine kinases, STK). A few protein kinases have dual specificity and phosphorylate threonine and tyrosine residues. Almost all kinases contain a similar 250–300 amino acid catalytic domain. The N-terminal domain, which contains subdomains I–IV, generally folds into a two-lobed structure which binds and orients the ATP (or GTP) donor molecule. The larger C terminal lobe, which contains subdomains VI A-XI, binds the protein substrate and carries out the transfer of the gamma phosphate from ATP to the hydroxyl group of a serine, threonine, or tyrosine residue. Subdomain V spans the two lobes.

The kinases may be categorized into families by the different amino acid sequences (generally between 5 and 100 residues) located on either side of, or inserted into loops of, the kinase domain. These added amino acid sequences allow the regulation of each kinase as it recognizes and interacts with its target protein. The primary structure of the kinase domains is conserved and can be further subdivided into 11 subdomains. Each of the 11 subdomains contain specific residues and motifs or patterns of amino acids that are characteristic of that subdomain and are highly conserved (Hardie, G. and Hanks, S. (1995) *The Protein Kinase Facts Books*, I and II, Academic Press, San Diego, Calif.).

The second messenger dependent protein kinases primarily mediate the effects of second messengers such as cyclic AMP (cAMP) cyclic GMP, inositol triphosphate, phosphatidylinositol, 3,4,5-triphosphate, cyclic ADP vibose, arachidonic acid and diacylglycerol. The cyclic-AMP dependent protein kinases (PKA) are important members of the STK family. Cyclic-AMP is an intracellular mediator of hormone action in all procaryotic and animal cells that have been studied. Such hormone-induced cellular responses include thyroid hormone secretion, cortisol secretion, progesterone secretion, glycogen breakdown, bone resorption, and regulation of heart rate and force of heart muscle contraction. PKA is found in all animal cells and is thought to account for the effects of cyclic-AMP in most of these cells. Altered PKA expression is implicated in a variety of disorders and diseases including; cancer, thyroid disorders, diabetes, atherosclerosis, and cardiovascular disease (Isselbacher, K. J. et al. (1994) *Harrison's Principles of Internal Medicine*, McGraw-Hill, New York, N.Y.).

The mitogen-activated protein kinases (MAP) are also members of the STK family. MAP kinases also regulate intracellular signaling pathways. They mediate signal transduction from the cell surface to the nucleus via phosphorylation cascades. Several subgroups have been identified, and each manifests different substrate specificities and responds to distinct extracellular stimuli (Egan, S. E. and Weinberg, R. A. (1993) Nature 365:781–783). MAP kinase signaling pathways are present in mammalian cells as well as in yeast. The extracellular stimuli which activate mammalian pathways include epidermal growth factor (EGF), ultraviolet light, hyperosmolar medium, heat shock, endotoxic lipopolysaccharide (LPS), and pro-inflammatory cytokines such as tumor necrosis factor (TNF) and interleukin- 1 (IL-1). An important member of the MAP kinases is the cytoplasmic p70 ribosomal S6 kinase which is essential for the initiation of protein synthesis in all cell types following mitogenic stimulation (Hershey, J.W.B. (1989) J. Biol. Chem. 264:20823–26). Altered MAP kinase expression can therefore be implicated in a variety of disease conditions including cancer, inflammation, immune disorders, and disorders affecting growth and development.

A detailed understanding of kinase pathways and signal transduction suggest certain mechanisms for interceding in the progression of inflammatory illnesses and of uncontrolled cell proliferation. The novel kinases, polynucleotides which encode them, and antibodies binding to them satisfy a need in the art by providing compounds which are useful for studying signaling cascades in various cells and tissues, diagnosing disease, and selecting inhibitors or drugs which can potentially be used to treat various disorders or diseases in which altered kinase expression is implicated.

SUMMARY OF THE INVENTION

The present invention features two novel serine/threonine protein kinases hereinafter designated HSTK-1 and HSTK-2 and referred to collectively as HSTK (human serine/threonine kinases) characterized as having chemical and structural homology to two p70 S6 ribosomal kinases from man (GI 189508) and rabbit (GI 1562), and to a serine/threonine kinase from fetal liver (GI 1480861), and XEEK1, (GI 1016551), from the African frog, *Xenopus laevis*.

Accordingly, the invention features a substantially purified HSTK-1 having the amino acid sequence, SEQ ID NO:1. The invention also features substantially purified HSTK-2 having the amino acid sequence, SEQ ID NO:3.

One aspect of the invention features isolated and substantially purified polynucleotides that encode HSTK. In a particular aspect, the polynucleotides are the nucleotide sequences of SEQ ID NO:2 and SEQ ID NO:4.

The invention also relates to polynucleotide sequences comprising the complements of SEQ ID NO:2 and SEQ ID NO:4 or variants thereof. In addition, the invention features polynucleotide sequences which hybridize under stringent conditions to SEQ ID NO:2 and SEQ ID NO:4.

The invention additionally features nucleic acid sequences encoding polypeptides, oligonucleotides, peptide nucleic acids (PNA), fragments, portions or antisense molecules thereof, and expression vectors and host cells comprising polynucleotides that encode HSTK. The present invention also features antibodies which bind specifically to HSTK, and pharmaceutical compositions comprising substantially purified HSTK. The invention also features the use of agonists and antagonists of HSTK.

BRIEF DESCRIPTION OF THE FIGURES

FIGS. 1A and 1B show the amino acid sequence (SEQ ID NO:1) and nucleic acid sequence (SEQ ID NO:2) of HSTK-1. The alignment was produced using MacDNASIS PRO software (Hitachi Software Engineering Co., Ltd., San Bruno, Calif.).

FIGS. 2A, 2B and 2C show the amino acid sequence (SEQ ID NO:3) and nucleic acid sequence (SEQ ID NO:4) of HSTK-2.

FIG. 3 shows the amino acid sequence alignments between HSTK-1 (SEQ ID NO:1), the human STK (GI 1480861; SEQ ID NO:5), and XEET1 from Xenopus laevis (GI 1016651; SEQ ID NO:6). The alignment was produced using the multisequence alignment program of LASERGENE software (DNASTAR Inc, Madison Wis.).

FIGS. 4A and 4B show the amino acid alignments between HSTK-2 (SEQ ID NO:3), the human p70 S6, (GI 189508: SEQ ID NO:7), and the rabbit p70 S6 kinase (GI 1562; SEQ ID NO:8).

DESCRIPTION OF THE INVENTION

Figure 5:
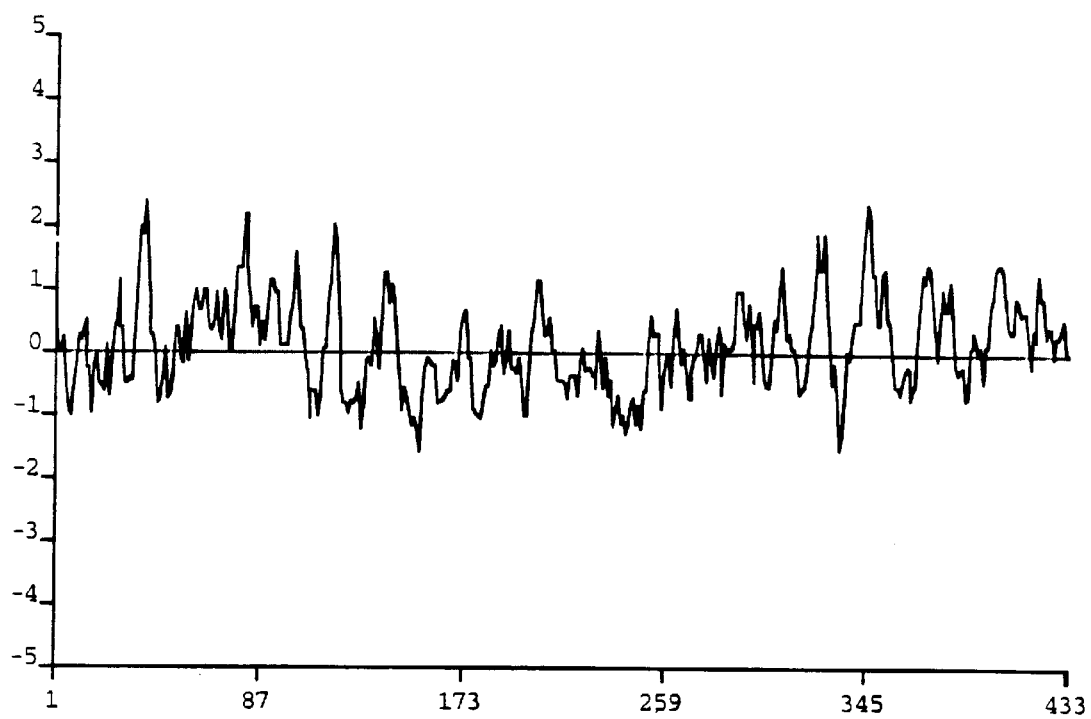
FIG. 5 shows the hydrophobicity plot (MacDNASIS PRO software) for HSTK-1, SEQ ID NO:1; the positive X axis reflects amino acid position, and the negative Y axis, hydrophobicity.

Before the present proteins, nucleotide sequences, and methods are described, it is understood that this invention is not limited to the particular methodology, protocols, cell lines, vectors, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

Definitions

"Nucleic acid sequence" as used herein refers to an oligonucleotide, nucleotide, or polynucleotide, and fragments or portions thereof, and to DNA or RNA of genomic or synthetic origin which may be single- or double-stranded, and represent the sense or antisense strand. Similarly, "amino acid sequence" as used herein refers to an oligopeptide, peptide, polypeptide, or protein sequence and fragments or portions thereof, of a naturally occurring or synthetic molecule.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

"Peptide nucleic acid", as used herein, refers to a molecule which comprises an oligomer to which an amino acid residue, such as lysine, and an amino group have been added. These small molecules, also designated anti-gene agents, stop transcript elongation by binding to their complementary strand of nucleic acid (Nielsen, P. E. et al. (1993) Anticancer Drug Des. 8:53–63).

HSTK, as used herein, refers to the amino acid sequences of substantially purified HSTK obtained from any species, particularly mammalian, including bovine, ovine, porcine, murine, equine, and preferably human, from any source whether natural, synthetic, semi-synthetic, or recombinant.

"Consensus", as used herein, refers to a nucleic acid sequence which has been resequenced to resolve uncalled bases, or which has been extended using XL-PCR Kit (Perkin Elmer, Norwalk, Conn.) in the 5' and/or the 3' direction and resequenced, or which has been assembled from the overlapping sequences of more than one Incyte clone using the GELVIEW Fragment Assembly system (GCG, Madison, Wis.), or which has been both extended and assembled.

A "variant" of HSTK, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both. Guidance in determining which amino acid residues may be substituted, inserted, or deleted without abolishing biological or immunological activity may be found using computer programs well known in the art, for example, LASERGENE software (DNASTAR).

A "deletion", as used herein, refers to a change in either amino acid or nucleotide sequence in which one or more amino acid or nucleotide residues, respectively, are absent.

An "insertion" or "addition", as used herein, refers to a change in an amino acid or nucleotide sequence resulting in the addition of one or more amino acid or nucleotide residues, respectively, as compared to the naturally occurring molecule.

A "substitution", as used herein, refers to the replacement of one or more amino acids or nucleotides by different amino acids or nucleotides, respectively.

The term "biologically active", as used herein, refers to a protein having structural, regulatory, or biochemical functions of a naturally occurring molecule. Likewise, "immunologically active" refers to the capability of the natural, recombinant, or synthetic HSTK, or any oligopeptide thereof, to induce a specific immune response in appropriate animals or cells and to bind with specific antibodies.

The term "agonist", as used herein, refers to a molecule which, when bound to HSTK, causes a change in HSTK which modulates the activity of HSTK. Agonists may include proteins, nucleic acids, carbohydrates, or any other molecules which bind to HSTK.

The terms "antagonist" or "inhibitor", as used herein, refer to a molecule which, when bound to HSTK, blocks the biological or immunological activity of HSTK. Antagonists and inhibitors may include proteins, nucleic acids, carbohydrates, or any other molecules which bind to HSTK.

The term "modulate", as used herein, refers to a change or an alteration in the biological activity of HSTK. Modulation may be an increase or a decrease in protein activity, a change in binding characteristics, or any other change in the biological, functional or immunological properties of HSTK.

The term "mimetic", as used herein, refers to a molecule, the structure of which is developed from knowledge of the structure of HSTK or portions thereof and, as such, is able to effect some or all of the actions of STK-like molecules.

The term "derivative", as used herein, refers to the chemical modification of a nucleic acid encoding HSTK or the encoded HSTK. Illustrative of such modifications would be replacement of hydrogen by an alkyl, acyl, or amino group. A nucleic acid derivative would encode a polypeptide which retains essential biological characteristics of the natural molecule.

The term "substantially purified", as used herein, refers to nucleic or amino acid sequences that are removed from their natural environment, isolated or separated, and are at least 60% free, preferably 75% free, and most preferably 90% free from other components with which they are naturally associated.

"Amplification" as used herein refers to the production of additional copies of a nucleic acid sequence and is generally carried out using polymerase chain reaction (PCR) technologies well known in the art (Dieffenbach, C. W. and G. S. Dveksler (1995) *PCR Primer. a Laboratory Manual*, Cold Spring Harbor Press, Plainview, N.Y.).

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen binds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., membranes, filters, chips, pins or glass slides to which cells have been fixed for in situ hybridization).

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands.

The term "homology", as used herein, refers to a degree of complementarity. There may be partial homology or complete homology (i.e., identity). A partially complementary sequence is one that at least partially inhibits an identical sequence from hybridizing to a target nucleic acid; it is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding, the probe will not hybridize to the second non-complementary target sequence.

As known in the art, numerous equivalent conditions may be employed to comprise either low or high stringency conditions. Factors such as the length and nature (DNA, RNA, base composition) of the sequence, nature of the target (DNA, RNA, base composition, presence in solution or immobilization, etc.), and the concentration of the salts and other components (e.g., the presence or absence of formamide, dextran sulfate and/or polyethylene glycol) are considered and the hybridization solution may be varied to generate conditions of either low or high stringency different from, but equivalent to, the above listed conditions.

The term "stringent conditions", as used herein, is the "stringency" which occurs within a range from about Tm-5° C. (5° C. below the melting temperature (Tm) of the probe) to about 20° C. to 25° C. below Tm. As will be understood by those of skill in the art, the stringency of hybridization may be altered in order to identify or detect identical or related polynucleotide sequences.

The term "antisense", as used herein, refers to nucleotide sequences which are complementary to a specific DNA or RNA sequence. The term "antisense strand" is used in reference to a nucleic acid strand that is complementary to the "'sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block either the further transcription or translation. In this manner, mutant phenotypes may be generated. The designation "negative" is sometimes used in reference to the antisense strand, and "positive" is sometimes used in reference to the sense strand.

The term "portion", as used herein, with regard to a protein (as in "a portion of a given protein") refers to fragments of that protein. The fragments may range in size from four amino acid residues to the entire amino acid sequence minus one amino acid. Thus, a protein "comprising at least a portion of the amino acid sequence of SEQ ID NO:1 or SEQ ID NO:3" encompasses the full-length human HSTK and fragments thereof.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "antigenic determinant", as used herein, refers to that portion of a molecule that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The terms "specific binding" or "specifically binding", as used herein, in reference to the interaction of an antibody and a protein or peptide, mean that the interaction is dependent upon the presence of a particular structure (i.e., the antigenic determinant or epitope) on the protein; in other words, the antibody is recognizing and binding to a specific protein structure rather than to proteins in general. For example, if an antibody is specific for epitope "A", the presence of a protein containing epitope A (or free, unlabeled A) in a reaction containing labeled "A" and the antibody will reduce the amount of labeled A bound to the antibody.

The term "sample", as used herein, is used in its broadest sense. A biological sample suspected of containing nucleic acid encoding HSTK or fragments thereof may comprise a cell, chromosomes isolated from a cell (e.g., a spread of metaphase chromosomes), genomic DNA (in solution or bound to a solid support such as for Southern analysis), RNA (in solution or bound to a solid support such as for northern analysis), cDNA (in solution or bound to a solid support), an extract from cells or a tissue, and the like.

The term "correlates with expression of a polynucleotide", as used herein, indicates that the detection of the presence of ribonucleic acid that is similar to SEQ ID NO:2 or SEQ ID NO:4 by northern analysis is indicative of the presence of mRNA encoding HSTK in a sample and thereby correlates with expression of the transcript from the polynucleotide encoding the protein.

"Alterations" in the polynucleotide of SEQ ID NO:2 or SEQ ID NO:4, as used herein, comprise any alteration in the sequence of polynucleotides encoding HSTK including deletions, insertions, and point mutations that may be detected using hybridization assays. Included within this definition is the detection of alterations to the genomic DNA sequence which encodes HSTK (e.g., by alterations in the pattern of restriction fragment length polymorphisms capable of hybridizing to SEQ ID NO:2 or SEQ ID NO:4), the inability of a selected fragment of SEQ ID NO:2 or SEQ ID NO:4 to hybridize to a sample of genomic DNA (e.g., using allele-specific oligonucleotide probes), and improper or unexpected hybridization, such as hybridization to a locus other than the normal chromosomal locus for the polynucleotide sequence encoding HSTK (e.g., using fluorescent in situ hybridization [FISH] to metaphase chromosomes spreads).

As used herein, the term "antibody" refers to intact molecules as well as fragments thereof, such as Fa, F(ab')$_2$, and Fv, which are capable of binding the epitopic determinant. Antibodies that bind HSTK polypeptides can be prepared using intact polypeptides or fragments containing small peptides of interest as the immunizing antigen. The polypeptide or peptide used to immunize an animal can be derived from translated RNA or synthesized chemically, and can be conjugated to a carrier protein, if desired. Commonly used carriers that are chemically coupled to peptides include bovine serum albumin and thyroglobulin. The coupled peptide is then used to immunize the animal (e.g., a mouse, a rat, or a rabbit).

The term "humanized antibody", as used herein, refers to antibody molecules in which amino acids have been replaced in the non-antigen binding regions in order to more closely resemble a human antibody, while still retaining the original binding ability.

The Invention

The invention is based on the discovery of two novel human serine/threonine protein kinases, HSTK-1 and HSTK-2, the polynucleotides encoding HSTK-1 and HSTK-2, and the use of these compositions for the diagnosis, prevention, or treatment of cancer, inflammatory diseases, and growth and development disorders.

Nucleic acids encoding the human HSTK-1 of the present invention were first identified in Incyte Clone 1285444 from the colon cDNA library (COLNNOT16) through a computer-generated search for amino acid sequence alignments. An associated tumor tissue indicating an invasive grade 2 adenocarcinoma of the colon was isolated from the same patient. A consensus sequence, SEQ ID NO:2, was derived from the following overlapping and/or extended nucleic acid sequences: Incyte Clones 640515 and 899424/ BRSTTUT03, 759781/ BRAITUT02, 128544/ COLNNOT16, 1530036/ PANCNOT04, 1498665/ SINTBST01, 674558/ CRBLNOT01, 1352857/ LATRTUT02, and 1308413/ COLNFET02.

Nucleic acids encoding the human HSTK-2 of the present invention were first identified in Incyte Clone 1309709 from the fetal small intestine cDNA library (COLNFET02) through a computer-generated search for amino acid sequence alignments. A consensus sequence, SEQ ID NO:4, was derived from the following overlapping and/or extended nucleic acid sequences: Incyte Clones 1251853/ LUNGFET03, 1309709/ COLNFET02, 1377014/ LUNGNOT10, 1574640 and 1577736/ LNODNOT03, and 1629855/ COLNPOT01.

Figure 6:
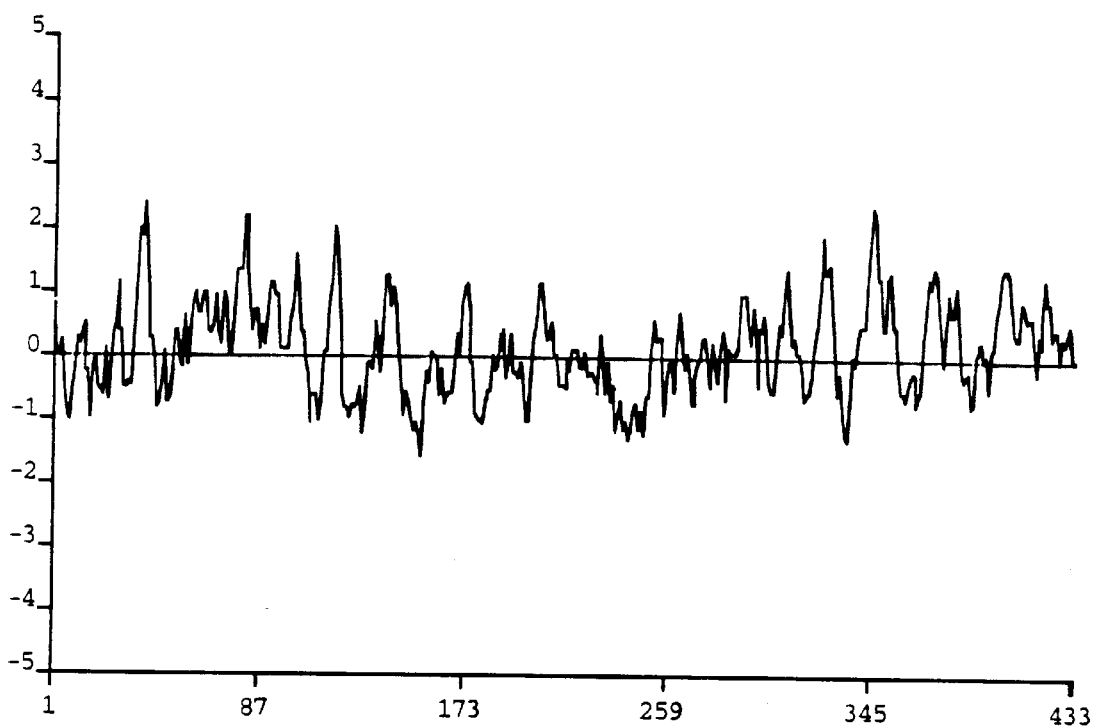
FIG. 6 shows the hydrophobicity plot for GI 1480861, SEQ ID NO:5.
Figure 7:
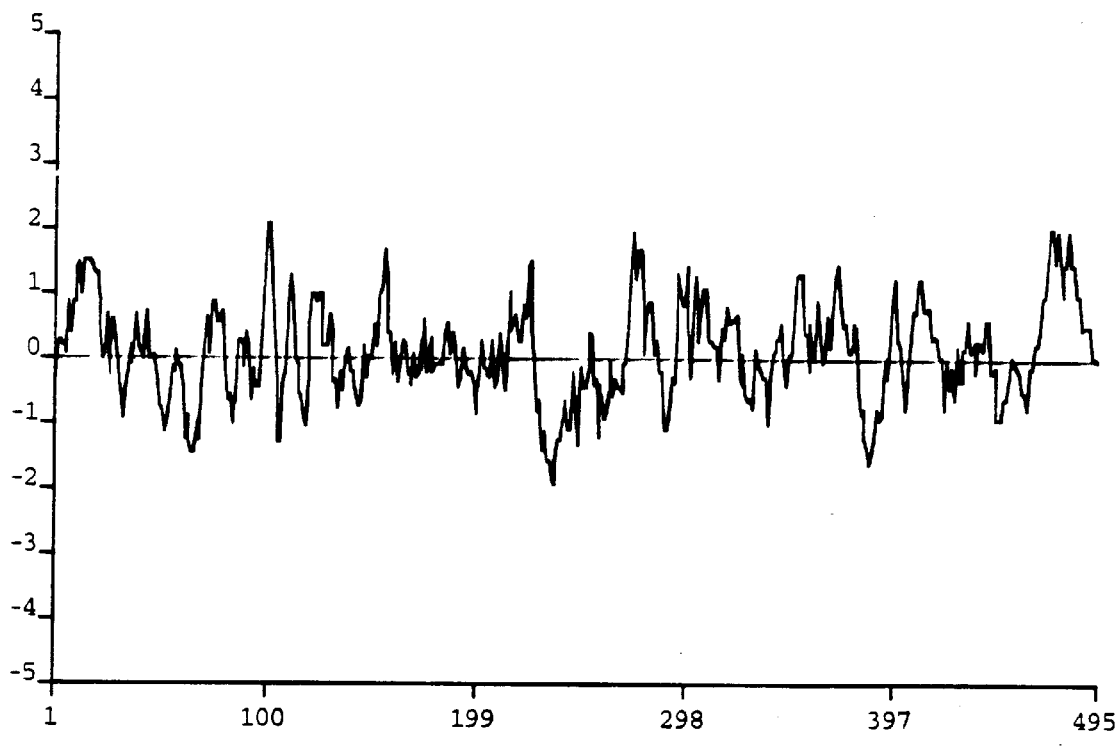
FIG. 7 shows the hydrophobicity plot for HSTK-2, SEQ ID NO:3.
Figure 8:
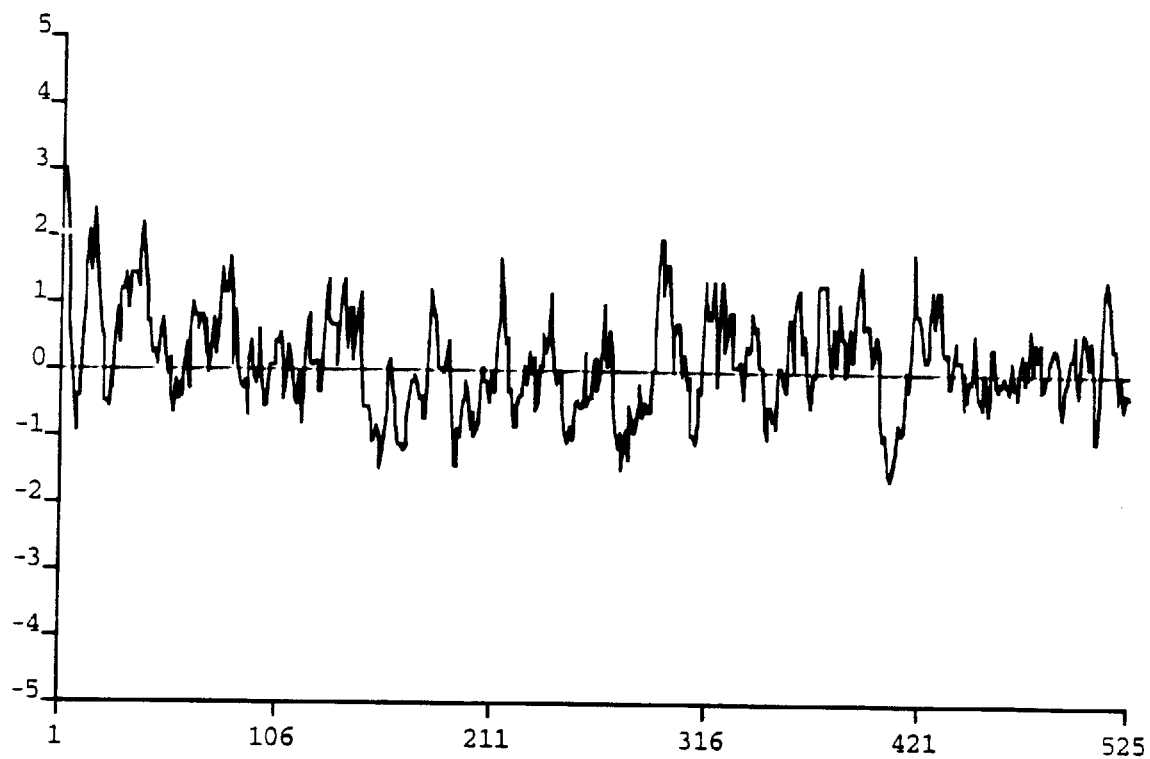
FIG. 8 shows the hydrophobicity plot for GI 189508, SEQ ID NO:7.

In one embodiment, the invention encompasses the novel human HSTK-1, a polypeptide comprising the amino acid sequence of SEQ ID NO:1, as shown in FIGS. 1A and 1B. HSTK-1 is 433 amino acids in length and has potential glycosylation sites at N247 and N393. Cysteine residues representing potential intramolecular cysteine-cysteine disulfide linkage sites are found at residues C73, C132, C134, C151, C158, C210, C278, C391, and C418. As shown in FIG. 3, HSTK-1 has chemical and structural homology with human STK (GI 1480861; SEQ ID NO:5) and with XEEK1 from the african frog (GI 1016551; SEQ ID NO:6) (Su, J. Y. et al. (1996) J. Biol. Chem. 271:14430–37). HSTK-1 shares 92% identity with the human STK and 82% identity with the frog STK. In addition, each of the three proteins share certain amino acid sequence motifs that are characteristic of protein kinases as a whole and of STKs in particular (Source: Hardie, G. and Hanks, S., supra). The sequence GXGXXGXV found in subdomain I of the catalytic domain of many protein kinases is found beginning at G55 for HSTK-1. The residues K78 and E98 form an ion pair in many protein kinases and are found in the same relative positions in all three proteins. Known phosphorylation sites for STKs are found at positions T189 and T212. The nine cysteine residues in HSTK-1 are also conserved in one or both of the other STKs. As illustrated by FIGS. 5 and 6, HSTK-1 and GI 1480861 have rather similar hydrophobicity plots. Partial cDNAs encoding a portion of HSTK-1 are found in a number of tumors including those of brain, breast, and heart. Fetal colon is also a source for partial transcripts of HSTK-1, as fetal liver is the source for GI 1480861.

Figure 4A:
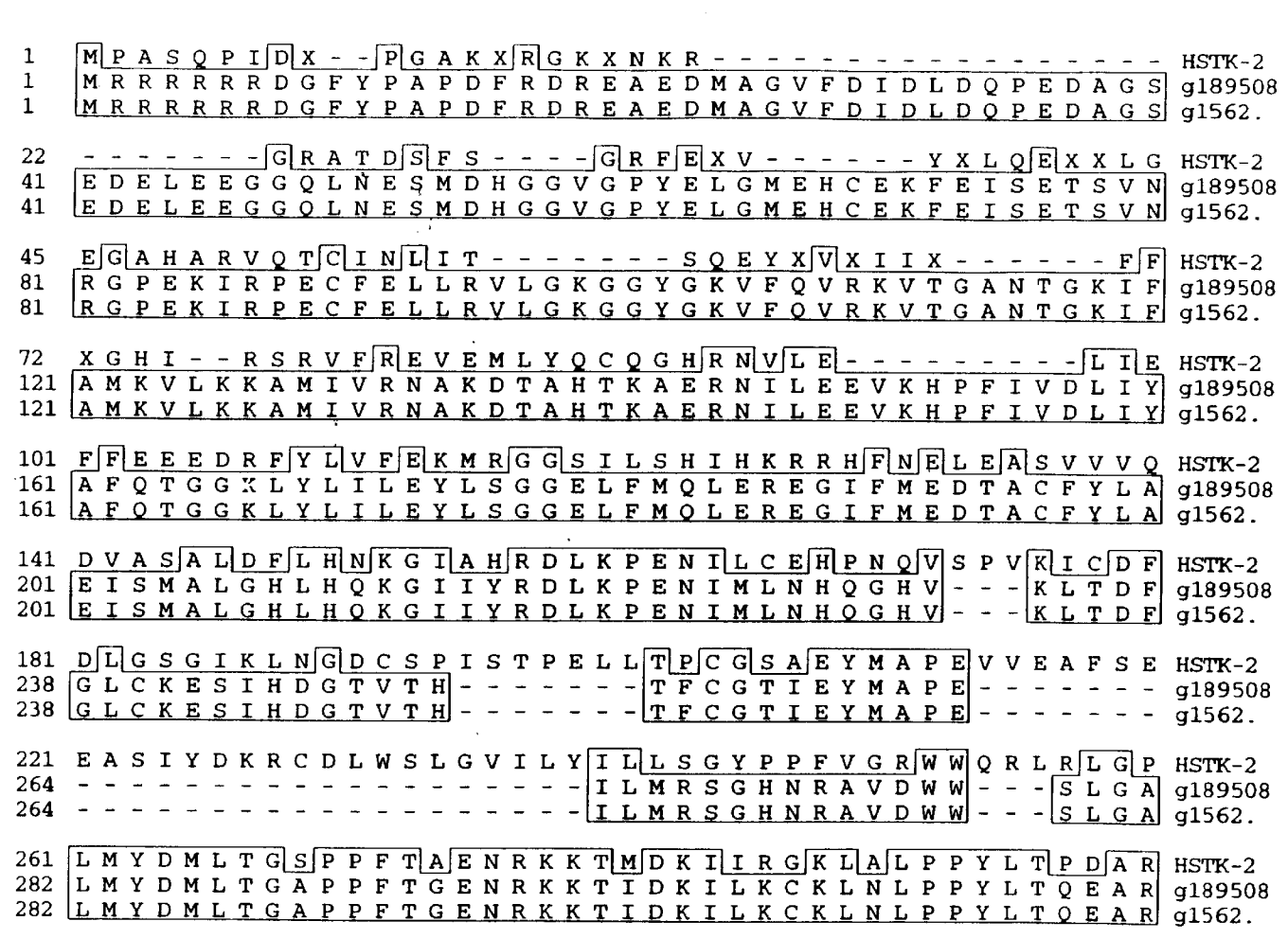

Another embodiment of the invention encompasses the novel human HSTK-2, a polypeptide comprising the amino acid sequence of SEQ ID NO:3, as shown in FIGS. 2A, 2B, and 2C. HSTK-2 is 495 amino acids in length and has a potential glycosylation site at N(310). Cysteine residues representing potential intramolecular cysteine-cysteine disulfide linkage sites are found at residues C54, C89, C166, C178, C192, C204, C229, and C351. As shown in FIG. 4, HSTK-1 has chemical and structural homology with the human and rabbit STK, p70 S6, G1 189508 (SEQ ID NO:7) and GI 1562 (SEQ ID NO:8), respectively. HSTK has approximately 40% overall identity with each of the two STKs shown, but also shares numerous sequence motifs characteristic of STKs. The sequence (H/YRDLKXXN found in subdomain VIB of the catalytic domain of many protein kinases is found beginning at H(156) for HSTK-2 and is conserved in GI 189508 and GI 1562 as well. A number of individual amino acid residues which have been identified as relatively invariant in STKs are shared between HSTK-2 and the other two STKs shown (Kozma S. C. et al. (1990) Proc. Natl. Acad. Sci. USA 87:7365–69). These residues are: D(179), F(180), S(243), G(259), and R(314). Three serine autophosphorylation sites, which are characteristic of the p70 S6 STKs, are also shared by the three molecules at S(413), S(420), and S(426). An autoinhibitory sequence, KEKFSFEPPKIR, which is believed to inhibit binding of the p70 S6 STK to the S6 ribosomal substrate is also found beginning at K(402) for HSTK-2 and is reasonably conserved in this molecule (Hardie, G. and Hanks, S., supra). Cysteine residues C54 and C204 are also conserved in each of the three molecules. Partial transcripts of the gene encoding HSTK-2 are found in only 5 libraries with a 60% (3/5) occurrence in cDNA libraries from fetal tissues (colon and lung) and a 40% (2/5) occurrence in lymph nodes.

The invention also encompasses HSTK variants. A preferred HSTK variant is one having at least 80%, and more preferably 90%, amino acid sequence similarity to the HSTK amino acid sequence (SEQ ID NO:1 or SEQ ID NO:3). A most preferred HSTK variant is one having at least 95% amino acid sequence similarity to SEQ ID NO:1 or SEQ ID NO:3.

The invention also encompasses polynucleotides which encode HSTK. Accordingly, any nucleic acid sequence which encodes the amino acid sequence of HSTK can be used to generate recombinant molecules which express HSTK. In a particular embodiment, the invention encompasses the polynucleotide comprising the nucleic acid of SEQ ID NO:2 or SEQ ID NO:4 as shown in FIG. 1 and FIG. 2, respectively.

It will be appreciated by those skilled in the art that as a result of the degeneracy of the genetic code, a multitude of nucleotide sequences encoding HSTK, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring HSTK, and all such variations are to be considered as being specifically disclosed.

Although nucleotide sequences which encode HSTK and its variants are preferably capable of hybridizing to the nucleotide sequence of the naturally occurring HSTK under appropriately selected conditions of stringency, it may be advantageous to produce nucleotide sequences encoding HSTK or its derivatives possessing a substantially different codon usage. Codons may be selected to increase the rate at which expression of the peptide occurs in a particular prokaryotic or eukaryotic expression host in accordance with the frequency with which particular codons are utilized by the host. Other reasons for substantially altering the nucleotide sequence encoding HSTK and its derivatives without altering the encoded amino acid sequences include the production of RNA transcripts having more desirable properties, such as a greater half-life, than transcripts produced from the naturally occurring sequence.

The invention also encompasses production of a DNA sequence, or portions thereof, which encode HSTK and its derivatives, entirely by synthetic chemistry. After production, the synthetic gene may be inserted into any of the many available DNA vectors and cell systems using reagents that are well known in the art at the time of the filing of this application. Moreover, synthetic chemistry may be used to introduce mutations into a sequence encoding HSTK or any portion thereof.

Also encompassed by the invention are polynucleotide sequences that are capable of hybridizing to the claimed nucleotide sequences, and in particular, those shown in SEQ ID NO:2 and SEQ ID NO:4, under various conditions of stringency. Hybridization conditions are based on the melting temperature (Tm) of the nucleic acid binding complex or probe, as taught in Kimmel, A. R. (1987; Methods Enzymol. Vol. 152), and may be used at a defined stringency.

Altered nucleic acid sequences encoding HSTK which are encompassed by the invention include deletions, insertions, or substitutions of different nucleotides resulting in a polynucleotide that encodes the same or a functionally equivalent HSTK. The encoded protein may also contain deletions, insertions, or substitutions of amino acid residues which produce a silent change and result in a functionally equivalent HSTK. Deliberate amino acid substitutions may be made on the basis of similarity in polarity, charge, solubility, hydrophobicity, hydrophilicity, and/or the amphipathic nature of the residues as long as the biological activity of HSTK is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine; phenylalanine and tyrosine.

Also included within the scope of the present invention are alleles of the gene encoding HSTK. As used herein, an "allele" or "allelic sequence" is an alternative form of the gene which may result from at least one mutation in the nucleic acid sequence. Alleles may result in altered mRNAs or polypeptides whose structure or function may or may not be altered. Any given gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

Methods for DNA sequencing which are well known and generally available in the art may be used to practice any embodiments of the invention. The methods may employ such enzymes as the Klenow fragment of DNA polymerase I, SEQUENASE (US Biochemical Corp, Cleveland, Ohio), Taq polymerase (Perkin Elmer), thermostable T7 polymerase (Amersham, Pharmacia Biotech, Piscataway N.J.), or combinations of recombinant polymerases and proofreading exonucleases such as the ELONGASE Amplification System marketed by Life Technologies (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Me.) and the ABI 377 DNA sequencers (Perkin Elmer).

The polynucleotide sequence encoding HSTK may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2:318–322). In particular, genomic DNA is first amplified in the presence of primer to linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16:8186). The primers may be designed using OLIGO® 4.06 Primer Analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1:111–119). In this method, multiple restriction enzyme digestions and ligations may also be used to place an engineered double-stranded sequence into an unknown portion of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PROMOTERFINDER libraries (Clontech, Palo Alto, Calif.) to walk in genomic DNA. This process avoids the need to screen libraries and may be is useful in finding intron/exon junctions.

When screening for full-length cDNAs, it is preferable to use libraries that have been size-selected to include larger cDNAs. Also, random-primed libraries are preferable in that they will contain more sequences which contain the 5' regions of genes. Use of a randomly primed library may be especially preferable for situations in which an oligo d(T) library does not yield a full-length cDNA. Genomic libraries may be useful for extension of sequence into the 5' and 3' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled device camera. Output/light intensity may be converted to electrical signal using appropriate software (e.g. GENOTYPER and SEQUENCE NAVIGATOR, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode HSTK, or fusion proteins or functional equivalents thereof, may be used in recombinant DNA molecules to direct expression of HSTK in appropriate host cells. Due to the inherent degeneracy of the genetic code, other DNA sequences which encode substantially the same or a functionally equivalent amino acid sequence may be produced and these sequences may be used to clone and express HSTK.

As will be understood by those of skill in the art, it may be advantageous to produce HSTK-encoding nucleotide sequences possessing non-naturally occurring codons. For example, codons preferred by a particular prokaryotic or eukaryotic host can be selected to increase the rate of protein expression or to produce a recombinant RNA transcript having desirable properties, such as a half-life which is longer than that of a transcript generated from the naturally occurring sequence.

The nucleotide sequences of the present invention can be engineered using methods generally known in the art in order to alter the HSTK coding sequence for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequence. For example, site-directed mutagenesis may be used to insert new restriction sites, alter glycosylation patterns, to change codon preference, to produce splice variants, or other mutations, and so forth.

In another embodiment of the invention, a natural, modified, or recombinant polynucleotide encoding HSTK may be ligated to a heterologous sequence to encode a fusion protein. For example, to screen peptide libraries for inhibitors of HSTK activity, it may be useful to encode a chimeric HSTK protein that can be recognized by a commercially available antibody. A fusion protein may also be engineered to contain a cleavage site located between a HSTK encoding sequence and the heterologous protein sequence, so that HSTK may be cleaved and purified away from the heterologous moiety.

In another embodiment, the coding sequence of HSTK may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the HSTK amino acid sequence, or a portion thereof. For example, peptide synthesis can be performed using various solid-phase techniques (Roberge, J. Y. et al. (1995) Science 269:202–204) and automated synthesis may be achieved, for example, using the ABI 431 A Peptide Synthesizer (Perkin Elmer).

The newly synthesized peptide may be substantially purified by preparative high performance liquid chromatography (e.g., Creighton, T. (1983) *Proteins, Structures and Molecular Principles*, WH Freeman and Co., New York, N.Y.). The composition of the synthetic peptides may be confirmed by amino acid analysis or sequencing (e.g., the Edman degradation procedure; Creighton, supra). Additionally, the amino acid sequence of HSTK, or any part thereof, may be altered during direct synthesis and/or combined using chemical methods with sequences from other proteins, or any part thereof, to produce a variant polypeptide.

In order to express a biologically active HSTK, the nucleotide sequence encoding HSTK or functional equivalents, may be inserted into an appropriate expression vector, i.e., a vector which contains the necessary elements for the transcription and translation of the inserted coding sequence.

Methods which are well known to those skilled in the art may be used to construct expression vectors containing a HSTK coding sequence and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual*, Cold Spring Harbor Press, Plainview, N.Y., and Ausubel, F. M. et al. (1989) *Current Protocols in Molecular Biology*, John Wiley & Sons, New York, N.Y.

A variety of expression vector/host systems may be utilized to contain and express a HSTK coding sequence. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems.

The "control elements" or "regulatory sequences" are those non-translated regions of the vector—enhancers, promoters, 5' and 3' untranslated regions—which interact with host cellular proteins to carry out transcription and translation. Such elements may vary in their lo strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, LaJolla, Calif.) or pSport1 plasmid (Life Technologies) and ptrp-lac hybrids, and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding HSTK, vectors based on SV40 or EBV may be used with an appropriate selectable marker.

In bacterial systems, a number of expression vectors may be selected depending upon the use intended for HSTK. For example, when large quantities of HSTK are needed for the induction of antibodies, vectors which direct high level expression of fusion proteins that are readily purified may be used. Such vectors include, but are not limited to, the multifunctional *E. coli* cloning and expression vectors such as BLUESCRIPT (Stratagene), in which the sequence encoding HSTK may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomyces cerevisiae*, a number of vectors containing constitutive or inducible promoters such as alpha factor, alcohol oxidase, and PGH may be used. For reviews, see Ausubel et al. (supra) and Grant et al. (1987) Methods Enzymol. 153:516–544.

In cases where plant expression vectors are used, the expression of a sequence encoding HSTK may be driven by any of a number of promoters. For example, viral promoters such as the 35S and 19S promoters of CaMV may be used alone or in combination with the omega leader sequence from TMV (Takamatsu, N. (1987) EMBO J. 6:307–311). Alternatively, plant promoters such as the small subunit of RUBISCO or heat shock promoters may be used (Coruzzi, G. et al. (1984) EMBO J. 3:1671–1680; Broglie, R. et al. (1984) Science 224:838–843; Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196).

An insect system may also be used to express HSTK. For example, in one such system, *Autographa californica* nuclear polyhedrosis virus (AcNPV) is used as a vector to express foreign genes in *Spodoptera frugiperda* cells or in Trichoplusia larvae. The sequence encoding HSTK may be cloned into a non-essential region of the virus, such as the polyhedrin gene, and placed under control of the polyhedrin promoter. Successful insertion of HSTK will render the polyhedrin gene inactive and produce recombinant virus lacking coat protein. The recombinant viruses may then be used to infect, for example, *S. frugiperda* cells or Trichoplusia larvae in which HSTK may be expressed (Engelhard, E. K. et al. (1994) Proc. Nat. Acad. Sci. 91:3224–3227).

In mammalian host cells, a number of viral-based expression systems may be utilized. In cases where an adenovirus is used as an expression vector, a sequence encoding HSTK may be ligated into an adenovirus transcription/translation complex consisting of the late promoter and tripartite leader sequence. Insertion in a non-essential E1 or E3 region of the viral genome may be used to obtain a viable virus which is capable of expressing HSTK in infected host cells (Logan, J. and Shenk, T. (1984) Proc. Natl. Acad. Sci. 81:3655–3659). In addition, transcription enhancers, such as the Rous sarcoma virus (RSV) enhancer, may be used to increase expression in mammalian host cells.

Specific initiation signals may also be used to achieve more efficient translation of a sequence encoding HSTK. Such signals include the ATG initiation codon and adjacent sequences. In cases where sequences encoding HSTK, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and WI38, which have specific cellular machinery and characteristic mechanisms for such post-translational activities, may be chosen to ensure the correct modification and processing of the foreign protein.

For long-term, high-yield production of recombinant proteins, stable expression is preferred. For example, cell lines which stably express HSTK may be transformed using expression vectors which may contain viral origins of replication and/or endogenous expression elements and a selectable marker gene on the same or separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–23) genes which can be employed in tk⁻ or aprt⁻ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77:3567–70); npt, which confers resistance to the aminoglycosides neomycin and G-418 (Colbere-Garapin, F. et al (1981) J. Mol. Biol. 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85:8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55:121–131).

Although the presence/absence of marker gene expression suggests that the gene of interest is also present, its presence and expression may need to be confirmed. For example, if the sequence encoding HSTK is inserted within a marker gene sequence, recombinant cells containing sequences encoding HSTK can be identified by the absence of marker gene function. Alternatively, a marker gene can be placed in tandem with a sequence encoding HSTK under the control of a single promoter. Expression of the marker gene in response to induction or selection usually indicates expression of the tandem gene as well.

Alternatively, host cells which contain the coding sequence for HSTK and express HSTK may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of the nucleic acid or protein.

The presence of the polynucleotide sequence encoding HSTK can be detected by DNA-DNA or DNA-RNA hybridization or amplification using probes or portions or fragments of polynucleotides encoding HSTK. Nucleic acid amplification based assays involve the use of oligonucleotides or oligomers based on the HSTK-encoding sequence to detect transformants containing DNA or RNA encoding HSTK. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides, which can be used as a probe or amplimer.

A variety of protocols for detecting and measuring the expression of HSTK, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on HSTK is preferred, but a competitive binding assay may be employed. These and other assays are described, among other places, in Hampton, R. et al. (1990; *Serological Methods, a Laboratory Manual*, APS Press, St Paul, Minn.) and Maddox, D. E. et al. (1983) J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding HSTK include oligolabeling, nick translation, end-labeling or PCR amplification using a labeled nucleotide. Alternatively, the sequence encoding HSTK, or any portion of it, may be cloned into a vector for the production of an mRNA probe.

Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits Amersham Pharmacia Biotech, Promega, and U.S. Biochemical Corp., Cleveland, Ohio). Suitable reporter molecules or labels, which may be used, include radionuclides, enzymes, fluorescent, chemiluminescent, or chromogenic agents as well as substrates, cofactors, inhibitors, magnetic particles, and the like.

Host cells transformed with a nucleotide sequence encoding HSTK may be cultured under conditions suitable for the expression and recovery of the protein from cell culture. The protein produced by a recombinant cell may be secreted or contained intracellularly depending on the sequence and/or the vector used. As will be understood by those of skill in the art, expression vectors containing polynucleotides which encode HSTK may be designed to contain signal sequences which direct secretion of HSTK through a prokaryotic or eukaryotic cell membrane. Other recombinant constructions may be used to join sequences encoding HSTK to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and HSTK may be used to facilitate purification. One such expression vector provides for expression of a fusion protein containing HSTK and a nucleic acid encoding 6 histidine residues preceding a thioredoxin or an enterokinase cleavage site. The histidine residues facilitate purification on IMIAC (immobilized metal ion affinity chromatography as described in Porath, J. et al. (1992, Prot. Exp. Purif. 3:263–281) while the enterokinase cleavage site provides a means for purifying HSTK from the fusion protein. A discussion of vectors which contain fusion proteins is provided in Kroll, D. J. et al. (1993; DNA Cell Biol. 12:441–453).

In addition to recombinant production, fragments of HSTK may be produced by direct peptide synthesis using solid-phase techniques (cf Stewart et al. (1969) *Solid-Phase Peptide Synthesis*, W.H. Freeman Co., San Francisco, Calif.; Merrifield J. (1963) J. Am. Chem. Soc. 85:2149–2154). Protein synthesis may be performed using manual techniques or by automation. Automated synthesis may be achieved, for example, using Applied Biosystems 431 A Peptide Synthesizer (Perkin Elmer). Various fragments of HSTK may be chemically synthesized separately and combined using chemical methods to produce the full length molecule Therapeutics The rationale for the use of nucleotide and polypeptide sequences disclosed herein is based in part on the chemical and structural homology among the novel HSTK and two p70 S6 ribosomal kinases from man (GI 189508) and rabbit (GI 1562), and a serine/threonine kinase from fetal liver (GI 1480861), and XEEK1, (GI 1016551) from the african frog. Because of the widespread roles for protein kinases in cell signaling processes in various cells and tissues, altered HPK expression may be implicated in a variety of disorders and diseases.

HSTK-1 bears homology to GI 1480861 and GI 1016651, which have been characterized as cyclic-AMP dependent protein kinases (PKA; Su, J. Y. et al., supra). Altered PKA expression has been associated with a number of disorders including cancer and cardiovascular disease (Isselbache,r K. J., supra). HSTK-1 has been shown to be associated with tumors of the brain, breast, and heart and may therefore be useful in the treatment of these and other cancers. In particular, increased expression of HSTK-1 may have a role in tumor promotion or growth, and therefore suppresssion of HSTK-1 activity may be useful in cancer treatment.

In one embodiment of the invention, inhibitors of HSTK-1, or vectors containing antisense sequences to HSTK-1 may be administered to a cancer patient in order to inhibit HSTK-1 activity and growth of the cancer. Administration of HSTK-1 inhibitors as a novel approach to cancer treatment may be especially useful in combination therapy with other therapeutic agents. Such combinations of therapeutic agents having different cellular mechanisms of action often have synergystic effects allowing the use of lower effective doses of each agent and lessening side effects.

HSTK-2 bears homology to the p70 S6 ribosomal kinases which are known to be essential in protein synthesis and cell proliferation. The occurrence of HSTK-2 in fetal tissues and lymphoid tissues suggests that it may be important in fetal growth and development and in the immune response. Immature development of various fetal organs and tissues results in adverse conditions in newborn infants such as respiratory distress syndrome, anemia, and infections due to lack to gamma globulin synthesis by lymphoid tissues. Accordingly, decreased expression of HSTK-2 appears be involved in disorders affecting growth and development while increased expression of HSTK-1 appears to be involved in immune disorders and inflammatory diseases such as asthma and arthritis.

In another embodiment of the invention, HSTK-2, derivatives thereof, or vectors expressing HSTK-2 may be used to treat conditions of respiratory distress or anemia.

In another embodiment of the invention, inhibitors of HSTK-2, antibodies to HSTK-2, or vectors expressing antisense sequences to HSTK-2 may be used to treat inflammatory diseases such as asthma or arthritis.

In another embodiment, antagonists which block or modulate the effect of HSTK may be used in those situations where such inhibition is therapeutically desirable. Such antagonists or inhibitors may be produced using methods which are generally known in the art, and include particularly the use of purified HSTK to produce antibodies or to screen libraries of pharmaceutical agents for those which specifically bind HSTK. For example, in one aspect, antibodies which are specific for HSTK may be used directly as an antagonist, or indirectly as a targeting or delivery mechanism for bringing a pharmaceutical agent to cells or tissue which express HSTK.

The antibodies may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with HSTK or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the peptides, fragments, or oligopeptides used to induce antibodies to HSTK have an amino acid sequence consisting of at least five amino acids, and more preferably at least 10 amino acids. It is also preferable that they are identical to a portion of the amino acid sequence of the natural protein, and they may contain the entire amino acid sequence of a small, naturally occurring molecule. Short stretches of HSTK amino acids may be fused with those of another protein such as keyhole limpet hemocyanin and antibody produced against the chimeric molecule.

Monoclonal antibodies to HSTK may be prepared using any technique which provides for the production of antibody molecules by continuous cell lines in culture. These include, but are not limited to, the hybridoma technique, the human B-cell hybridoma technique, and the EBV-hybridoma technique (Koehler et al. (1 975) Nature 256:495–497; Kosbor et al. (1983) Immunol. Today 4:72; Cote et al. (1983) Proc. Natl. Acad. Sci. 80:2026–2030; Cole et al. (1985) *Monoclonal Antibodies and Cancer Therapy*, Alan R. Liss Inc., New York, N.Y., pp. 77–96).

In addition, techniques developed for the production of "chimeric antibodies", the splicing of mouse antibody genes to human antibody genes to obtain a molecule with appropriate antigen specificity and biological activity can be used (Morrison et al. (1984) Proc. Natl. Acad. Sci. 81:6851–6855; Neuberger et al. (1984) Nature 312:604–608; Takeda et al. (1985) Nature 314:452–454). Alternatively, techniques described for the production of single chain antibodies may be adapted, using methods known in the art, to produce HSTK-specific single chain antibodies. Antibodies with related specificity, but of distinct idiotypic composition, may be generated by chain shuffling from random combinatorial immunoglobulin libraries (Burton D. R. (1991) Proc. Natl. Acad. Sci. 88:11120–3).

Antibodies may also be produced by inducing in vivo production in the lymphocyte population or by screening recombinant immunoglobulin libraries or panels of highly specific binding reagents as disclosed in the literature (Orlandi, et al. (1989) Proc. Natl. Acad. Sci. 86:3833–3837; Winter, G. et al. (1991) Nature 349:293–299).

Antibody fragments which contain specific binding sites for HSTK may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse et al. (1989) Science 256:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HSTK and its specific antibody. A two-site, monoclonal-based immunoassay utilizing monoclonal antibodies reactive to two non-interfering HSTK epitopes is preferred, but a competitive binding assay may also be employed (Maddox, supra).

In another embodiment of the invention, the polynucleotides encoding HSTK, or any fragment thereof, or antisense sequences, may be used for therapeutic purposes. In one aspect, antisense to the polynucleotide encoding HSTK may be used in situations in which it would be desirable to block the synthesis of the protein. In particular, cells may be transformed with sequences complementary to polynucleotides encoding HSTK. Thus, antisense sequences may be used to modulate HSTK activity, or to achieve regulation of gene function. Such technology is now well known in the art, and sense or antisense oligomers or larger fragments, can be designed from various locations along the coding or control regions of sequences encoding HSTK.

Expression vectors derived from retroviruses, adenovirus, herpes or vaccinia viruses, or from various bacterial plasmids may be used for delivery of nucleotide sequences to the targeted organ, tissue or cell population. Methods which are well known to those skilled in the art can be used to construct recombinant vectors which will express antisense polynucleotides of the gene encoding HSTK. These techniques are described both in Sambrook et al. (supra) and in Ausubel et al. (supra).

Genes encoding HSTK can be turned off by transforming a cell or tissue with expression vectors which express high levels of a polynucleotide or fragment thereof which encodes HSTK. Such constructs may be used to introduce untranslatable sense or antisense sequences into a cell. Even in the absence of integration into the DNA, such vectors may continue to transcribe RNA molecules until all copies are disabled by endogenous nucleases. Transient expression may last for a month or more with a non-replicating vector and even longer if appropriate replication elements are part of the vector system.

As mentioned above, modifications of gene expression can be obtained by designing antisense molecules, DNA, RNA, or PNA, to the control regions of the gene encoding HSTK, i.e., the promoters, enhancers, and introns. Oligonucleotides derived from the transcription initiation site, e.g., between positions –10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches*, Futura Publishing Co., Mt. Kisco, N.Y.). The antisense molecules may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding HSTK.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro and in vivo transcription of DNA sequences encoding HSTK. Such DNA sequences may be incorporated into a wide variety of vectors with suitable RNA polymerase promoters such as T7 or SP6. Alternatively, these cDNA constructs that synthesize antisense RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection and by liposome injections may be achieved using methods which are well known in the art.

Any of the therapeutic methods described above may be applied to any suitable subject including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of HSTK, antibodies to HSTK, mimetics, agonists, antagonists, or inhibitors of HSTK. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of HSTK, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example HSTK or fragments thereof, antibodies of HSTK, agonists, antagonists or inhibitors of HSTK, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind HSTK may be used for the diagnosis of conditions or diseases characterized by expression of HSTK, or in assays to monitor patients being treated with HSTK, agonists, antagonists or inhibitors. The antibodies useful for diagnostic purposes may be prepared in the same manner as those described above for therapeutics. Diagnostic assays for HSTK include methods which utilize the antibody and a label to detect HSTK in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring HSTK are known in the art and provide a basis for diagnosing altered or abnormal levels of HSTK expression. Normal or standard values for HSTK expression are established by combining body fluids or cell extracts taken from normal mammalian subjects, preferably human, with antibody to HSTK under conditions suitable for complex formation. The amount of standard complex formation may be quantified by various methods, but preferably by photometric means. Quantities of HSTK expressed in subject, control, and disease, samples from biopsied tissues are compared with the standard values. Deviation between standard and subject values establishes the parameters for diagnosing disease.

In another embodiment of the invention, the polynucleotides encoding HSTK may be used for diagnostic purposes. The polynucleotides which may be used include oligonucleotide sequences, antisense RNA and DNA molecules, and PNAs. The polynucleotides may be used to detect and quantitate gene expression in biopsied tissues in which expression of HSTK may be correlated with disease. The diagnostic assay may be used to distinguish between absence, presence, and excess expression of HSTK, and to monitor regulation of HSTK levels during therapeutic intervention.

In one aspect, hybridization with PCR probes which are capable of detecting polynucleotide sequences, including genomic sequences, encoding HSTK or closely related molecules, may be used to identify nucleic acid sequences which encode HSTK. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding HSTK, alleles, or related sequences.

Probes may also be used for the detection of related sequences, and should preferably contain at least 50% of the nucleotides from any of the HSTK encoding sequences. The hybridization probes of the subject invention may be DNA or RNA and derived from the nucleotide sequence of SEQ ID NO:2 or from genomic sequence including promoter, enhancer elements, and introns of the naturally occurring HSTK.

Means for producing specific hybridization probes for DNAs encoding HSTK include the cloning of nucleic acid sequences encoding HSTK or HSTK derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding HSTK may be used for the diagnosis of conditions or diseases which are associated with expression of HSTK. Examples of such conditions or diseases include cancers of the brain, breast and heart, inflammatory diseases such as asthma and arthritis, and disorders affecting growth and development such as respiratory distress and anemia. The polynucleotide sequences encoding HSTK may be used in Southern or northern analysis, dot blot, or other membrane-based technologies; in PCR technologies; or in dip stick, pin, ELISA or chip assays utilizing fluids or tissues from patient biopsies to detect altered HSTK expression. Such qualitative or quantitative methods are well known in the art.

In a particular aspect, the nucleotide sequences encoding HSTK may be useful in assays that detect activation or induction of various cancers, particularly those mentioned above. The nucleotide sequence encoding HSTK may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequence has hybridized with nucleotide sequences in the sample, and the presence of altered levels of nucleotide sequences encoding HSTK in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of HSTK, a normal or standard profile for expression is established. This may be accomplished by combining body fluids or cell extracts taken from normal subjects, either animal or human, with a sequence, or a fragment thereof, which encodes HSTK, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides encoding HSTK may involve the use of PCR. Such oligomers may be chemically synthesized, generated enzymatically, or produced from a recombinant source. Oligomers will preferably consist of two nucleotide sequences, one with sense orientation (5'->3') and another with antisense (3'<-5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of HSTK include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 229–236). The speed of quantitation of multiple samples may be accelerated by running the assay in an ELISA format where the oligomer of interest is presented in various dilutions and a spectrophotometric or colorimetric response gives rapid quantitation.

In another embodiment of the invention, the nucleic acid sequence which encodes HSTK may also be used to generate hybridization probes which are useful for mapping the naturally occurring genomic sequence. The sequence may be mapped to a particular chromosome or to a specific region of the chromosome using well known techniques. Such techniques include FISH, FACS, or artificial chromosome constructions, such as yeast artificial chromosomes, bacterial artificial chromosomes, bacterial P1 constructions or single chromosome cDNA libraries as reviewed in Price, C. M. (1993) Blood Rev. 7:127–134, and Trask, B. J. (1991) Trends Genet. 7:149–154.

FISH (as described in Verma et al. (1988) *Human Chromosomes: A Manual of Basic Techniques*, Pergamon Press, New York, N.Y.) may be correlated with other physical chromosome mapping techniques and genetic map data. Examples of genetic map data can be found in the 1994 Genome Issue of Science (265:1981). Correlation between the location of the gene encoding HSTK on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22-23 (Gatti, R. A. et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, HSTK, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between HSTK and the agent being tested, may be measured.

Another technique for drug screening which may be used provides for high throughput screening of compounds having suitable binding affinity to the protein of interest as described in published PCT application W084/03564. In this method, as applied to HSTK large numbers of different small test compounds are synthesized on a solid substrate, such as plastic pins or some other surface. The test compounds are reacted with HSTK, or fragments thereof, and washed. Bound HSTK is then detected by methods well known in the art. Purified HSTK can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HSTK specifically compete with a test compound for binding HSTK. In this manner, the antibodies can be used to detect the presence of any peptide which shares one or more antigenic determinants with HSTK.

In additional embodiments, the nucleotide sequences which encode HSTK may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I Description of Tissues and cDNA Library Construction

The COLNNOT16 cDNA library was constructed from microscopically normal sigmoidal colon tissue removed from a 62-year-old Caucasian male during a sigmoidectomy. After presenting with blood in his stool, the patient was diagnosed with a malignant neoplasm in the cecum. The pathology report indicated an invasive grade 2 adenocarcinoma invading through the muscularis propria into the underlying adipose tissue. A single tubular adenoma with low grade dysplasia was located near the surgical margin of excision. One of ten mesenteric lymph nodes contained metastatic carcinoma, and extra nodal extension was identified. The patient history included hyperlipidemia, dermatitis, benign hypertension, atherosclerosis, and an episode of acute myocardial infarction. In addition, the patient had also undergone permanent colostomy, cholecystectomy, and repair of indirect inguinal hernia. There was a family history of malignant breast neoplasm in the mother, and malignant prostate cancer in a sibling.

The COLNFET02 cDNA library was constructed from colon tissue obtained from a 20-week-old Caucasian female fetus. The pregnant mother was treated with erythromycin for seven days in the first trimester for bronchitis (specimen #RU95-10-0739; IIAM, Exton, Pa.). In both the COLNNOT16 and COLNFET02 libraries, frozen tissue was homogenized and lysed using a Brinkmann Homogenizer Polytron PT-3000 (Brinkmann Instruments, Westbury, N.J.) in guanidinium isothiocyanate solution. The lysate was centrifuged over a 5.7 M CsCl cushion using a Beckman SW28 rotor in a Beckman L8-70M Ultracentrifuge (Beckman Coulter, Fullerton Calif.) for 18 hours at 25,000 rpm at ambient temperature. The RNA was extracted with acid phenol pH 4.7, precipitated using 0.3 M sodium acetate and 2.5 volumes of ethanol, resuspended in RNAse-free water, and DNase treated at 37% C The RNA extraction was repeated with acid phenol pH 4.7 and precipitated with sodium acetate and ethanol as before. The mRNA was then isolated using the QLIGOTEX kit (QIAGEN, Inc., Chatsworth, Calif.) and used to construct the cDNA library.

The mRNA was handled according to the recommended protocols in the SUPERSCRIPT Plasmid System for cDNA Synthesis and Plasmid Cloning (Cat. #18248-013, Life Technologies). The commercial plasmid pSPORT 1 (Life Technologies) was digested with EcoR I restriction enzyme (New England Biolabs, Beverley, Me.). The overhanging ends of the plasmid were filled in using Klenow enzyme (New England Biolabs) and 2'-deoxynucleotide 5'-triphosphates (dNTPs). The plasmid was self-ligated and transformed into the bacterial host, *E. coli* strain JM 109. An intermediate plasmid produced by the bacteria failed to digest with EcoR I confirming the desired loss of the EcoR I restriction site.

This intermediate plasmid (pSPORT 1-ERI) was then digested with Hind III restriction enzyme (New England Biolabs) and the overhang was filled in with Klenow and dNTPs. A 10-mer linker of sequence 5'. . . CGGAATTCCG . . . 3' was phosphorylated and ligated onto the blunt ends. The product of the ligation reaction was digested with EcoR I and self-ligated. Following transformation into JM109 host cells, plasmids were isolated and screened for the digestability with EcoR I but not with Hind III. The resulting plasmid designated pINCY, was tested for its ability to incorporate cDNAs using Not I and EcoR I restriction enzymes.

cDNAs were fractionated on a SEPHAROSE CL4B column (Cat. #275105-01, Amersham Pharmacia Biotech), and those cDNAs exceeding 400 bp were ligated into pINCY I. The plasmid pINCYCincyte Pharmaceuticals Palo Alto, Calif. was subsequently transformed into DH5α competent cells (Cat. #18258-012, Life Technologies).

II Isolation and Sequencing of cDNA Clones

Plasmid DNA was released from the cells and purified using the REAL Prep 96 Plasmid Kit (Catalog #26173, QIAGEN, Inc.). This kit enabled the simultaneous purification of 96 samples in a 96-well block using multi-channel reagent dispensers. The recommended protocol was employed except for the following changes: 1) the bacteria were cultured in 1 ml of sterile Terrific Broth (Catalog #22711, Life Technologies) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4% C The cDNAs were sequenced by the method of Sanger et al. (1975, J. Mol. Biol. 94:441f), using a Hamilton Micro Lab 2200 (Hamilton, Reno, Nev.) in combination with Peltier Thermal Cyclers (PTC200 from MJ Research, Watertown, Me.) and Applied Biosystems 377 DNA Sequencing Systems; and the reading frame was determined.

IV Homology Searching of cDNA Clones and Their Deduced Proteins

Each cDNA was compared to sequences in GenBank using a search algorithm developed by Applied Biosystems and incorporated into the INHERIT 670 sequence analysis system. In this algorithm, Pattern Specification Language (TRW Inc, Los Angeles, Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT- 670 sequence analysis system using the methods similar to those used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul, S. F. (1993) J. Mol. Evol. 36:290–300; Altschul et al. (1990) J. Mol. Biol. 215:403–410), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

V Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul, S. F. 1993 and 1990, supra) are used to search for identical or related molecules in nucleotide databases such as Gen-Bank or the LIFESEQ database (Incyte Pharmaceuticals). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding HSTK occurs. Abundance and percent abundance are also reported. Abundance directly reflects the number of times a particular transcript is represented in a cDNA library, and percent abundance is abundance divided by the total number of sequences examined in the cDNA library.

VI Extension of HSTK-Encoding Polynucleotides to Full Length or to Recover Regulatory Sequences Full length HSTK-encoding nucleic acid sequence (SEQ ID NO:2 or SEQ ID NO:4) is used to design oligonucleotide primers for extending a partial nucleotide sequence to full length or for obtaining 5' or 3', intron or other control sequences from genomic libraries. One primer is synthesized to initiate extension in the antisense direction (XLR) and the other is synthesized to extend sequence in the sense direction (XLF). Primers are used to facilitate the extension of the known sequence "outward" generating amplicons containing new, unknown nucleotide sequence for the region of interest. The initial primers are designed from the cDNA using OLIGO 4.06 (National Biosciences), or another appropriate program, to be 22–30 nucleotides in length, to have a GC content of 50% or more, and to anneal to the target sequence at temperatures about 68%–72% C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; M. J. Research, Watertown, Me.) and the following parameters:

Step 1 94% C for 1 min (initial denaturation)
Step 2 65% C for 1 min
Step 3 68% C for 6 min
Step 4 94% C for 15 sec
Step 5 65% C for 1 min
Step 6 68% C for 7 min
Step 7 Repeat step 4–6 for 15 additional cycles
Step 8 94% C for 15 sec
Step 9 65% C for 1 min
Step 10 68% C for 7:15 min
Step 11 Repeat step 8–10 for 12 cycles
Step 12 72% C for 8 min
Step 13 4% C (and holding)

A 5–10 &1 aliquot of the reaction mixture is analyzed by electrophoresis on a low concentration (about 0.6–0.8%) agarose mini-gel to determine which reactions were successful in extending the sequence. Bands thought to contain the largest products are selected and removed from the gel. Further purification involves using a commercial gel extraction method such as the QIAQUICK kit (QIAGEN Inc., Chatsworth, Calif.). After recovery of the DNA, Klenow enzyme is used to trim single-stranded, nucleotide overhangs creating blunt ends which facilitate religation and cloning.

After ethanol precipitation, the products are redissolved in 13 &1 of ligation buffer, 1&1 T4-DNA ligase (15 units) and 1&1 T4 polynucleotide kinase are added, and the mixture is incubated at room temperature for 2–3 hours or overnight at 16% C. Competent E. coli cells (in 40 &1 of appropriate media) are transformed with 3 &1 of ligation mixture and cultured in 80 &1 of SOC medium (Sambrook et al., supra). After incubation for one hour at 37% C, the whole transformation mixture is plated on Luria Bertani (LB)-agar (Sambrook et al., supra) containing 2×Carb. The following day, several colonies are randomly picked from each plate and cultured in 150 &1 of liquid LB/2×Carb medium placed in an individual well of an appropriate, commercially-available, sterile 96-well microtiter plate. The following day, 5 &I of each overnight culture is transferred into a non-sterile 96-well plate and after dilution 1:10 with water, 5 &1 of each sample is transferred into a PCR array.

For PCR amplification, 18 &1 of concentrated PCR reaction mix (3.3×) containing 4 units of rTth DNA polymerase, a vector primer, and one or both of the gene specific primers used for the extension reaction are added to each well. Amplification is performed using the following conditions:

Step 1 94% C for 60 sec

Step 2 94% C for 20 sec

Step 3 55% C for 30 sec

Step 4 72% C for 90 sec

Step 5 Repeat steps 2–4 for an additional 29 cycles

Step 6 72% C for 180 sec

Step 7 4% C (and holding)

Aliquots of the PCR reactions are run on agarose gels together with molecular weight markers. The sizes of the PCR products are compared to the original partial cDNAs, and appropriate clones are selected, ligated into plasmid, and sequenced.

VII Labeling and Use of Hybridization Probes

Hybridization probes derived from SEQ ID NO:2 or SEQ ID NO:4 are employed to screen cDNAs, genomic DNAs, or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 250 mCi of $[-^{32}P]$ adenosine triphosphate (Amersham Pharmacia Biotech) and T4 polynucleotide kinase (DuPont NEN®, Boston, Mass.). The labeled oligonucleotides are substantially purified with SEPHADEX G-25 superfine resin column (Amersham Pharmacia Biotech). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I Xba 1, or Pvu II; DuPont NEN®).

The DNA from each digest is fractionated on a 0.7 percent agarose gel and transferred to nylon membranes (Nytran Plus, Schleicher & Schuell, Durham, N.H.). Hybridization is carried out for 16 hours at 40% C. To remove nonspecific signals, blots are sequentially washed at room temperature under increasingly stringent conditions up to 0.1×saline sodium citrate and 0.5% sodium dodecyl sulfate. After XOMAT AR film (Eastman Kodak Rochester, N.Y.) is exposed to the blots in a Phosphoimager cassette (Molecular Dynamics, Sunnyvale, Calif.) for several hours, hybridization patterns are compared visually.

VIII Antisense Molecules

Antisense molecules to the HSTK-encoding sequence, or any part thereof, is used to inhibit in vivo or in vitro expression of naturally occurring HSTK. Although use of antisense oligonucleotides, comprising about 20 base-pairs, is specifically described, essentially the same procedure is used with larger cDNA fragments. An oligonucleotide based on the coding sequences of HSTK, as shown in FIG. 1, is used to inhibit expression of naturally occurring HSTK. The complementary oligonucleotide is designed from the most unique 5' sequence as shown in FIG. 1 and used either to inhibit transcription by preventing promoter binding to the upstream nontranslated sequence or translation of an HSTK-encoding transcript by preventing the ribosome from binding. Using an appropriate portion of the signal and 5' sequence of SEQ ID NO:2 or SEQ ID NO:4, an effective antisense oligonucleotide includes any 15–20 nucleotides spanning the region which translates into the signal or 5' coding sequence of the polypeptide as shown in FIGS. 1A and 1B and FIGS. 2A, 2B, and 2C.

IX Expression of HSTK

Expression of HSTK is accomplished by subcloning the cDNAs into appropriate vectors and transforming the vectors into host cells. In this case, the cloning vector, pSPORT1 (Life Technologies), previously used for the generation of the cDNA library is used to express HSTK in E. coli. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of HSTK into the bacterial growth media which can be used directly in the following assay for activity.

X Demonstration of HSTK Activity

HSTK activity may be measured by phosphorylation of a protein substrate using gamma-labeled $^{32}P$-ATP and quantitation of the incorporated radioactivity using a gamma radioisotope counter. For identification of p70 S6 ribosomal kinase activity, specifically, purified 40 S ribosomal protein is used as substrate (Flotow, H. and Thomas, G. (1992) J. Biol. Chem. 267:3074–78). HSTK is incubated with the protein substrate, $^{32}P$-ATP, and a kinase buffer. The $^{32}P$ incorporated into the substrate is then separated from free $^{32}P$-ATP by electrophoresis and the incorporated $^{32}P$ is counted. A determination of the specific amino acid residues phosphorylated is made by phosphoamino acid analysis of the hydrolyzed protein as described by Boyle, W. J. et al (1991) Methods in Enzymol. 201:110–148.

XI Production of HSTK Specific Antibodies

HSTK that is substantially purified using PAGE electrophoresis (Sambrook, supra), or other purification techniques, is used to immunize rabbits and to produce antibodies using standard protocols. The amino acid sequence deduced from SEQ ID NO:2 is analyzed using LASERGENE software (DNASTAR Inc) to determine regions of high immunogenicity and a corresponding oligopolypeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems Peptide Synthesizer Model 431A using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XII Purification of Naturally Occurring HSTK Using Specific Antibodies

Naturally occurring or recombinant HSTK is substantially purified by immunoaffinity chromatography using antibodies specific for HSTK. An immunoaffinity column is constructed by covalently coupling HSTK antibody to an activated chromatographic resin, such as CnBr-activated SEPHAROSE (Amersham Pharmacia Biotech). After the coupling, the resin is blocked and washed according to the manufacturer's instructions.

Media containing HSTK is passed over the immunoaffinity column, and the column is washed under conditions that allow the preferential absorbance of HSTK (e.g., high ionic strength buffers in the presence of detergent). The column is eluted under conditions that disrupt antibody/HSTK binding (eg, a buffer of pH 2–3 or a high concentration of a chaotrope, such as urea or thiocyanate ion), and HSTK is collected.

XIII Identification of Molecules Which Interact with HSTK

HSTK or biologically active fragments thereof are labeled with $^{125}I$ Bolton-Hunter reagent (Bolton et al. (1973) Biochem. J. 133:529). Candidate molecules previously arrayed in the wells of a multi-well plate are incubated with the labeled HSTK, washed and any wells with labeled HSTK complex are assayed. Data obtained using different concentrations of HSTK are used to calculate values for the number, affinity, and association of HSTK with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified nucleic acid molecule consisting of SEQ ID NO:2.

2. A hybridization probe comprising the isolated and purified nucleic acid molecule of claim 1.

3. An expression vector containing the nucleic acid molecule of claim 1.

4. A host cell containing the expression vector of claim 3.

5. A method for producing a polypeptide comprising the amino acid sequence of SEQ ID NO:1, the method comprising the steps of:
 a) culturing the host cell of claim 4 under conditions suitable for the expression of the polypeptide; and
 b) recovering the polypeptide from the host cell culture.

6. An isolated and purified nucleic acid molecule which is completely complementary to SEQ ID NO:2.

* * * * *

```
                              SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
          (A) LENGTH: 433 amino acids
          (B) TYPE: amino acid
          (C) STRANDEDNESS: single
          (D) TOPOLOGY: linear (vii) IMMEDIATE SOURCE:
          (B) CLONE: Consensus (xi) SEQUENCE DESCRIPTION: SEQ ID NO:1:

Met Glu Val Val Asp Pro Gln Gln Leu Gly Met Phe Thr Glu Gly Glu
 1               5                  10                  15

Leu Met Ser Val Gly Met Asp Thr Phe Ile His Arg Ile Asp Ser Thr
            20                  25                  30

Glu Val Ile Tyr Gln Pro Arg Arg Lys Arg Ala Lys Leu Ile Gly Lys
        35                  40                  45

Tyr Leu Met Gly Asp Leu Leu Gly Glu Gly Ser Tyr Gly Lys Val Lys
    50                  55                  60

Glu Val Leu Asp Ser Glu Thr Leu Cys Arg Arg Ala Val Lys Ile Leu
65                  70                  75                  80

Lys Lys Lys Lys Leu Arg Arg Ile Pro Asn Gly Glu Ala Asn Val Lys
                85                  90                  95

Lys Glu Ile Gln Leu Leu Arg Arg Leu Arg His Lys Asn Val Ile Gln
            100                 105                 110

Leu Val Asp Val Leu Tyr Asn Glu Glu Lys Gln Lys Met Tyr Met Val
        115                 120                 125
```

```
Met Glu Tyr Cys Val Cys Gly Met Gln Glu Met Leu Asp Ser Val Pro
            130                 135                 140
Glu Lys Arg Phe Pro Val Cys Gln Ala His Gly Tyr Phe Cys Gln Leu
145                 150                 155                 160
Ile Asp Gly Xaa Gly Tyr Leu His Xaa Gln Gly Ile Val His Lys Gly
                165                 170                 175
Ile Lys Pro Gly Asn Leu Leu Thr Thr Gly Thr Leu Lys Ile
            180                 185                 190
Ser Asp Leu Gly Val Ala Glu Ala Leu His Pro Phe Ala Ala Asp Asp
            195                 200                 205
Thr Cys Arg Thr Ser Gln Gly Ser Pro Ala Phe Gln Pro Pro Xaa Ile
            210                 215                 220
Ala Asn Gly Leu Asp Thr Phe Ser Gly Phe Lys Val Asp Ile Trp Ser
225                 230                 235                 240
Ala Gly Val Thr Leu Tyr Asn Ile Thr Thr Gly Leu Tyr Pro Phe Glu
                245                 250                 255
Gly Asp Asn Ile Tyr Lys Leu Phe Glu Asn Ile Gly Lys Gly Ser Tyr
            260                 265                 270
Ala Ile Pro Gly Asp Cys Gly Pro Pro Leu Ser Asp Leu Leu Lys Gly
            275                 280                 285
Met Leu Glu Tyr Glu Pro Ala Lys Arg Phe Ser Ile Arg Gln Ile Arg
            290                 295                 300
Gln His Ser Trp Phe Arg Lys Lys His Pro Pro Ala Glu Ala Pro Val
305                 310                 315                 320
Pro Ile Pro Pro Ser Pro Asp Thr Lys Asp Arg Trp Arg Arg Trp Thr
                325                 330                 335
Val Val Pro Tyr Leu Glu Asp Leu His Gly Ala Asp Glu Asp Glu Asp
                340                 345                 350
Leu Phe Asp Ile Glu Asp Asp Ile Ile Tyr Thr Gln Asp Phe Thr Val
            355                 360                 365
Pro Gly Gln Val Pro Glu Glu Glu Ala Ser His Asn Gly Gln Arg Arg
            370                 375                 380
Gly Leu Pro Lys Ala Val Cys Met Asn Gly Thr Glu Ala Gly Ala Val
385                 390                 395                 400
Ser Thr Lys Ser Arg Ala Glu Gly Arg Ala Pro Asn Pro Ala Arg Lys
                405                 410                 415
Ala Cys Ser Ala Ser Ser Lys Ile Arg Arg Leu Xaa Ala Cys Lys Gln
            420                 425                 430
Gln (2) INFORMATION FOR SEQ ID NO:2:

(i) SEQUENCE CHARACTERISTICS:
        (A) LENGTH: 1466 base pairs
        (B) TYPE: nucleic acid
        (C) STRANDEDNESS: single
        (D) TOPOLOGY: linear (vii) IMMEDIATE SOURCE:
        (B) CLONE: Consensus (xi) SEQUENCE DESCRIPTION: SEQ ID NO:2:

CTTTGTAAAA TTTTGGAGAA GGGAAGTNGG AACACAAGGA AGGACCGCTC ACCCGCGGAC      60

TCAGGGCTGG CGGCGGGACT CCAGGACCCT GGGTCCAGCA TGGAGGTGGT GGACCCGCAG     120

CAGCTGGGCA TGTTCACGGA GGGCGAGCTG ATGTCGGTGG GTATGGACAC GTTCATCCAC     180
```

```
CGNATCGACT CCACCGAGGT CATCTACCAG CCGCGCCGCA AGCGGGCCAA GCTCATCGGC    240

AAGTACCTGA TGGGGACCT GCTGGGGAA GGCTCTTACG GCAAGGTGAA GGAGGTGCTG     300

GACTCGGAGA CGCTGTGCAG GAGGGCCGTC AAGATCCTCA AGAAGAAGAA GTTGCGAAGG   360

ATCCCCAACG GGGAGGCCAA CGTGAAGAAG GAAATTCAAC TACTGAGGAG GTTACGGCAC   420

AAAAATGTCA TCCAGCTGGT GGATGTGTTA TACAACGAAG AGAAGCAGAA AATGTATATG   480

GTGATGGAGT ACTGCGTGTG TGGCATGCAG GAAATGCTGG ACAGCGTGCC GGAGAAGCGT   540

TTCCCAGTGT GCCAGGCCCA CGGGTACTTC TGTCAGCTGA TTGACGGCNT GGGGTACCTG   600

CATNGCCAGG GNATTGTGCA CAAGGGCATC AAGCCGGGGA ACCTGCTGCT CACCACCGGT   660

GGCACCCTCA AAATCTCCGA CCTGGGCGTG GCCGAGGCAC TGCACCCGTT CGCNGCGGAC   720

GACACCTGCC GGACCAGCCA GGGCTCCCCG GCTTTCCAGC CGCCCGANAT TGCCAACGGC   780

CTGGACACCT TCTCCGGCTT CAAGGTGGAC ATCTGGTCGG CTGGGGTCAC CCTCTACAAC   840

ATCACCACGG GTCTGTACCC CTTCGAAGGG GACAACATCT ACAAGTTGTT TGAGAACATC   900

GGGAAGGGGA GCTACGCCAT CCCGGGCGAC TGTGGCCCCC CGCTCTCTGA CCTGCTGAAA   960

GGGATGCTTG AGTACGAACC GGCCAAGAGG TTCTCCATCC GGCAGATCCG GCAGCACAGC  1020

TGGTTCCGGA AGAAACATCC TCCGGCTGAA GCACCAGTGC CCATCCCACC GAGCCCAGAC  1080

ACCAAGGACC GGTGGCGCAG ATGGACTGTG GTGCCGTACT TGGAGGACCT GCACGGCGCG  1140

GACGAGGACG AGGACCTCTT CGACATCGAG GATGACATCA TCTACACTCA GGACTTCACG  1200

GTGCCCGGAC AGGTCCCAGA AGAGGAGGCC AGTCACAATG GACAGCGCCG GGGCCTCCCC  1260

AAGGCCGTGT GTATGAACGG CACAGAGGCG GGCGCAGTGA GCACCAAATC CAGGGCGGAG  1320

GGCCGGGCCC CCAACCCTGC CCGCAAGGCC TGCTCCGCCA GCAGCAAGAT CCGCCGGCTG  1380

TNGGCCTGCA AGCAGCAGTG AGGCTGGCCG CCTGCAGCCC GTGTCCAGGA NCNCCGCCAG  1440

GTGNCGCNCC AGGCCCTCAG TCTTCC                                      1466
```

(2) INFORMATION FOR SEQ ID NO:3:

(i) SEQUENCE CHARACTERISTICS:
        (A) LENGTH: 495 amino acids
        (B) TYPE: amino acid
        (C) STRANDEDNESS: single
        (D) TOPOLOGY: linear (vii) IMMEDIATE SOURCE:
        (B) CLONE: Consensus (xi) SEQUENCE DESCRIPTION: SEQ ID NO:3:

```
Met Pro Ala Ser Gln Pro Ile Asp Xaa Pro Gly Ala Lys Xaa Arg Gly
 1               5                  10                  15

Lys Xaa Asn Lys Arg Gly Arg Ala Thr Asp Ser Phe Ser Gly Arg Phe
            20                  25                  30

Glu Xaa Val Tyr Xaa Leu Gln Glu Xaa Xaa Leu Gly Glu Gly Ala His
        35                  40                  45

Ala Arg Val Gln Thr Cys Ile Asn Leu Ile Thr Ser Gln Glu Tyr Xaa
    50                  55                  60

Val Xaa Ile Ile Xaa Phe Phe Xaa Gly His Ile Arg Ser Arg Val Phe
65                  70                  75                  80

Arg Glu Val Glu Met Leu Tyr Gln Cys Gln Gly His Arg Asn Val Leu
                85                  90                  95

Glu Leu Ile Glu Phe Phe Glu Glu Asp Arg Phe Tyr Leu Val Phe
                100                 105                 110
```

Glu Lys Met Arg Gly Gly Ser Ile Leu Ser His Ile His Lys Arg Arg
            115                 120                 125

His Phe Asn Glu Leu Glu Ala Ser Val Val Gln Asp Val Ala Ser
    130                 135                 140

Ala Leu Asp Phe Leu His Asn Lys Gly Ile Ala His Arg Asp Leu Lys
145                 150                 155                 160

Pro Glu Asn Ile Leu Cys Glu His Pro Asn Gln Val Ser Pro Val Lys
                165                 170                 175

Ile Cys Asp Phe Asp Leu Gly Ser Gly Ile Lys Leu Asn Gly Asp Cys
            180                 185                 190

Ser Pro Ile Ser Thr Pro Glu Leu Leu Thr Pro Cys Gly Ser Ala Glu
            195                 200                 205

Tyr Met Ala Pro Glu Val Val Glu Ala Phe Ser Glu Glu Ala Ser Ile
    210                 215                 220

Tyr Asp Lys Arg Cys Asp Leu Trp Ser Leu Gly Val Ile Leu Tyr Ile
225                 230                 235                 240

Leu Leu Ser Gly Tyr Pro Pro Phe Val Gly Arg Trp Trp Gln Arg Leu
                245                 250                 255

Arg Leu Gly Pro Leu Met Tyr Asp Met Leu Thr Gly Ser Pro Pro Phe
            260                 265                 270

Thr Ala Glu Asn Arg Lys Lys Thr Met Asp Lys Ile Ile Arg Gly Lys
    275                 280                 285

Leu Ala Leu Pro Pro Tyr Leu Thr Pro Asp Ala Arg Asp Leu Val Lys
290                 295                 300

Lys Phe Leu Lys Arg Asn Pro Ser Gln Arg Ile Gly Gly Gly Pro Gly
305                 310                 315                 320

Asp Ala Ala Asp Val Gln Arg His Pro Phe Phe Arg His Met Asn Trp
                325                 330                 335

Asp Asp Leu Leu Ala Trp Arg Val Asp Pro Pro Phe Arg Pro Cys Leu
            340                 345                 350

Gln Ser Glu Glu Asp Val Ser Gln Phe Asp Thr Arg Phe Thr Arg Gln
            355                 360                 365

Thr Pro Val Asp Ser Pro Asp Asp Thr Ala Leu Ser Glu Ser Ala Asn
    370                 375                 380

Gln Ala Phe Leu Gly Phe Thr Tyr Val Ala Pro Ser Val Leu Asp Ser
385                 390                 395                 400

Ile Lys Glu Gly Phe Ser Phe Gln Pro Lys Leu Arg Ser Pro Arg Arg
                405                 410                 415

Leu Asn Ser Ser Pro Arg Val Pro Val Ser Pro Leu Lys Phe Ser Pro
            420                 425                 430

Phe Glu Gly Phe Arg Pro Ser Pro Ser Leu Pro Glu Pro Thr Glu Leu
            435                 440                 445

Pro Leu Pro Pro Leu Leu Pro Pro Pro Pro Ser Thr Thr Ala Pro
    450                 455                 460

Leu Pro Ile Arg Pro Pro Ser Gly Thr Lys Lys Ser Lys Arg Gly Arg
465                 470                 475                 480

Gly Arg Pro Gly Arg Lys Pro Gly Gly Gly Glu Gly Ser Pro
                485                 490                 495

(2) INFORMATION FOR SEQ ID NO:4:

(i) SEQUENCE CHARACTERISTICS:
        (A) LENGTH: 1607 base pairs
        (B) TYPE: nucleic acid
        (C) STRANDEDNESS: single
        (D) TOPOLOGY: linear (vii) IMMEDIATE SOURCE:
    (B) CLONE: Consensus (xi) SEQUENCE DESCRIPTION: SEQ ID NO:4:

| | | | | | |
|---|---|---|---|---|---|
| GTATCNCTGC | CANGGNGGCC | CCCACCCNAA | ANCAGGGGGG | TNGGGCCGG | CCGGCCAGGG | 60 |
| CCATGTCCTG | AGNCCCCNNG | GCGTGCCTCC | TGGAACAGAT | ATGCCCGCCA | GCCAGCCCAT | 120 |
| TGACNTCCCG | GGCGCCAAGA | ANAGGGGCAA | GAANAATAAG | CGCGGCCGGG | CCACCGACAG | 180 |
| CTTCTCGGGC | AGGTTTGAAN | ACGTCTACCA | NCTGCAGGAA | NATNTGCTGG | GGGAGGGCGC | 240 |
| TCATGCCCGA | GTGCAGACCT | GCATTAACCT | GATCACCAGC | CAGGAGTACN | CCGTCAANAT | 300 |
| CATTGNTTTT | TTTNCAGGCC | ACATTCGGAG | CAGGGTTTTC | AGGGAGGTGG | AGATGCTGTA | 360 |
| CCAGTGCCAG | GGACACAGGA | ACGTCCTAGA | GCTGATTGAG | TTCTTCGAGG | AGGAGGACCG | 420 |
| CTTCTACCTG | GTGTTTGAGA | AGATGCGGGG | AGGCTCCATC | CTGAGCCACA | TCCACAAGCG | 480 |
| CCGGCACTTC | AACGAGCTGG | AGGCCAGCGT | GGTGGTGCAG | GACGTGGCCA | GCGCCTTGGA | 540 |
| CTTTCTGCAT | AACAAAGGCA | TCGCCCACAG | GGACCTAAAG | CCGGAAAACA | TCCTCTGTGA | 600 |
| GCACCCCAAC | CAGGTCTCCC | CCGTGAAGAT | CTGTGACTTC | GACCTGGGCA | GCGGCATCAA | 660 |
| ACTCAACGGG | GACTGCTCCC | CTATCTCCAC | CCCGGAGCTG | CTCACTCCGT | GCGGCTCGGC | 720 |
| GGAGTACATG | GCCCCGGAGG | TAGTGGAGGC | CTTCAGCGAG | GAGGCTAGCA | TCTACGACAA | 780 |
| GCGCTGCGAC | CTGTGGAGCC | TGGGCGTCAT | CTTGTATATC | CTACTCAGCG | GCTACCCGCC | 840 |
| CTTCGTGGGC | CGCTGGTGGC | AGCGACTGCG | GCTGGGACCG | CTGATGTACG | ACATGCTCAC | 900 |
| TGGATCGCCG | CCCTTTACCG | CAGAGAACCG | GAAGAAAACC | ATGGATAAGA | TCATCAGGGG | 960 |
| CAAGCTGGCA | CTNCCCCCCT | ACCTCACCCC | AGATGCCCGG | GACCTTGTCA | AAAAGTTTCT | 1020 |
| GAAACGGAAT | CCCAGCCAGC | GGATTGGGGG | TGGCCCAGGG | GATGCTGCTG | ATGTGCAGAG | 1080 |
| ACATCCCTTT | TTCCGGCACA | TGAATTGGGA | CGACCTTCTG | GCCTGGCGTG | TGGACCCCCC | 1140 |
| TTTCAGGCCC | TGTCTGCAGT | CAGAGGAGGA | CGTGAGCCAG | TTTGATACCC | GCTTCACACG | 1200 |
| GCAGACGCCG | GTGGACAGTC | CTGATGACAC | AGCCCTCAGC | GAGAGTGCCA | ACCAGGCCTT | 1260 |
| CCTGGGCTTC | ACATACGTGG | CGCCGTCTGT | CCTGGACAGC | ATCAAGGAGG | GCTTCTCCTT | 1320 |
| CCAGCCCAAG | CTGCGCTCAC | CCAGGCGCCT | CAACAGTAGC | CCCCGGGTCC | CCGTCAGCCC | 1380 |
| CCTCAAGTTC | TCCCCTTTTG | AGGGGTTTCG | GCCCAGCCCC | AGCCTGCCGG | AGCCCACGGA | 1440 |
| GCTACCTCTA | CCTCCACTCC | TGCCACCGCC | GCCGCCCTCG | ACCACCGCCC | CTCTCCCCAT | 1500 |
| CCGTCCCCCC | TCAGGGACCA | AGAAGTCCAA | GAGGGGCCGT | GGGCGTCCAG | GGCGTAGGAA | 1560 |
| GCCGGGTGGG | GGTGAGGGTA | GCCCTTGAGC | CCTGTCCCTG | CGGCTGT | | 1607 |

(2) INFORMATION FOR SEQ ID NO:5:

(i) SEQUENCE CHARACTERISTICS:
      (A) LENGTH: 433 amino acids
      (B) TYPE: amino acid
      (C) STRANDEDNESS: single
      (D) TOPOLOGY: linear (vii) IMMEDIATE SOURCE:
      (A) LIBRARY: GenBank
      (B) CLONE: 1480861

(xi) SEQUENCE DESCRIPTION: SEQ ID NO:5:

Met Glu Val Val Asp Pro Gln Gln Leu Gly Met Phe Thr Glu Gly Glu
 1               5                  10                  15

Leu Met Ser Val Gly Met Asp Thr Phe Ile His Arg Ile Asp Ser Thr
            20                  25                  30

-continued

```
Glu Val Ile Tyr Gln Pro Arg Arg Lys Arg Ala Lys Leu Ile Gly Lys
         35                  40                  45

Tyr Leu Met Gly Asp Leu Leu Gly Glu Gly Ser Tyr Gly Lys Val Lys
         50                  55                  60

Glu Val Leu Asp Ser Glu Thr Leu Cys Arg Arg Ala Val Lys Ile Leu
 65                  70                  75                  80

Lys Lys Lys Lys Leu Arg Arg Ile Pro Asn Gly Glu Ala Asn Val Lys
                     85                  90                  95

Lys Glu Ile Gln Leu Leu Arg Arg Leu Arg His Lys Asn Val Ile Gln
                 100                 105                 110

Leu Val Asp Val Leu Tyr Asn Glu Glu Lys Gln Lys Met Tyr Met Val
             115                 120                 125

Met Glu Tyr Cys Val Cys Gly Met Gln Glu Met Leu Asp Ser Val Pro
         130                 135                 140

Glu Lys Arg Phe Pro Val Cys Gln Ala His Gly Tyr Phe Cys Gln Leu
145                 150                 155                 160

Ile Asp Gly Leu Glu Tyr Leu His Ser Gln Gly Ile Val His Lys Asp
                 165                 170                 175

Ile Lys Pro Gly Asn Leu Leu Leu Thr Thr Gly Gly Thr Leu Lys Ile
             180                 185                 190

Ser Asp Leu Gly Val Ala Glu Ala Leu His Pro Phe Ala Ala Asp Asp
         195                 200                 205

Thr Cys Arg Thr Ser Gln Gly Ser Pro Ala Phe Gln Pro Pro Glu Ile
     210                 215                 220

Ala Asn Gly Leu Asp Thr Phe Ser Gly Phe Lys Val Asp Ile Trp Ser
225                 230                 235                 240

Ala Gly Val Thr Leu Tyr Asn Ile Thr Thr Gly Leu Tyr Pro Phe Glu
                 245                 250                 255

Gly Asp Asn Ile Tyr Lys Leu Phe Glu Asn Ile Gly Lys Gly Ser Tyr
             260                 265                 270

Ala Ile Pro Gly Asp Cys Gly Pro Pro Leu Ser Asp Leu Leu Lys Gly
         275                 280                 285

Met Leu Glu Tyr Glu Pro Ala Lys Arg Phe Ser Ile Arg Gln Ile Arg
     290                 295                 300

Gln His Ser Trp Phe Arg Lys Lys His Pro Pro Ala Glu Ala Pro Val
305                 310                 315                 320

Pro Ile Pro Pro Ser Pro Asp Thr Lys Asp Arg Trp Arg Ser Met Thr
                 325                 330                 335

Val Val Pro Tyr Leu Glu Asp Leu His Gly Ala Asp Glu Asp Glu Asp
             340                 345                 350

Leu Phe Asp Ile Glu Asp Asp Ile Ile Tyr Thr Gln Asp Phe Thr Val
         355                 360                 365

Pro Gly Gln Val Pro Glu Glu Ala Ser His Asn Gly Gln Arg Arg
     370                 375                 380

Gly Leu Pro Lys Ala Val Cys Met Asn Gly Thr Glu Ala Ala Gln Leu
385                 390                 395                 400

Ser Thr Lys Ser Arg Ala Glu Gly Arg Ala Pro Asn Pro Ala Arg Lys
                 405                 410                 415

Ala Cys Ser Ala Ser Ser Lys Ile Arg Arg Leu Ser Ala Cys Lys Gln
             420                 425                 430

Gln
```

(2) INFORMATION FOR SEQ ID NO:6:

(i) SEQUENCE CHARACTERISTICS:
    (A) LENGTH: 432 amino acids
    (B) TYPE: amino acid
    (C) STRANDEDNESS: single
    (D) TOPOLOGY: linear (vii) IMMEDIATE SOURCE:
    (A) LIBRARY: GenBank
    (B) CLONE: 1016651

(xi) SEQUENCE DESCRIPTION: SEQ ID NO:6:

```
Met Leu Cys Pro Ser Ser Met Asp Glu Glu Gly Ser Glu Ile Gly
 1               5                  10                  15

Phe Leu Gly Asp Leu Ser Val Gly Met Asp Thr Phe Ile His Arg Ile
             20                  25                  30

Asp Ser Thr Glu Val Ile Tyr Gln Pro Arg Arg Lys Arg Ala Lys Leu
             35                  40                  45

Val Gly Lys Tyr Leu Met Gly Asp Leu Gly Glu Gly Ser Tyr Gly
 50                  55                  60

Lys Val Lys Glu Met Leu Asp Ser Asp Thr Leu Cys Arg Arg Ala Val
 65                  70                  75                  80

Lys Ile Leu Lys Lys Lys Leu Arg Arg Ile Pro Asn Gly Glu Ala
             85                  90                  95

Asn Val Lys Lys Glu Ile Gln Leu Leu Arg Arg Leu Arg His Arg Asn
                100                 105                 110

Val Ile Gln Leu Val Asp Val Leu Tyr Asn Glu Glu Lys Gln Lys Met
            115                 120                 125

Tyr Met Val Met Glu Tyr Cys Val Cys Gly Met Gln Glu Met Leu Asp
            130                 135                 140

Ser Val Gln Asp Lys His Phe Pro Val Phe Gln Ala His Gly Tyr Phe
145                 150                 155                 160

Cys Gln Leu Ile Asp Gly Leu Glu Tyr Leu His Ser Gln Gly Ile Val
                165                 170                 175

His Lys Asp Ile Lys Pro Gly Asn Leu Leu Leu Thr Thr Asp Gly Thr
            180                 185                 190

Leu Lys Ile Ser Asp Leu Gly Val Ala Glu Ala Leu His Pro Phe Ala
            195                 200                 205

Glu Gly Asp Thr Cys Arg Thr Ser Gln Gly Ser Pro Ala Phe Gln Pro
210                 215                 220

Pro Glu Ile Ala Asn Gly Leu Asp Thr Phe Ser Gly Phe Lys Val Asp
225                 230                 235                 240

Ile Trp Ser Ala Gly Val Thr Leu Tyr Asn Ile Thr Thr Gly Leu Tyr
                245                 250                 255

Pro Phe Glu Gly Asp Asn Ile Tyr Lys Leu Phe Glu Asn Ile Gly Lys
            260                 265                 270

Gly Asp Tyr Ser Ile Pro Glu Glu Cys Gly Pro Leu Leu Ser Asp Leu
            275                 280                 285

Leu Arg Gly Met Leu Glu Tyr Asp Pro Ala Lys Arg Phe Ser Ile Gln
290                 295                 300

Gln Ile Arg Gln His Asn Trp Phe Arg Lys Lys His Pro His Met Asp
305                 310                 315                 320

Pro Ile Val Pro Ile Pro Pro Ser Pro Glu Thr Lys Asp Arg Trp Arg
                325                 330                 335

Ser Leu Thr Val Val Pro Tyr Leu Glu Asp Leu His Gly Tyr Ser Glu
            340                 345                 350
```

```
Glu Glu Asp Leu Cys Asp Phe Glu Asp Ile Ile Tyr Thr Gln Asp
        355                 360                 365

Phe Thr Val Pro Gly Gln Val Ala Glu Asp Tyr Phe Ala Gln Thr
        370                 375                 380

Gln Ser Thr Ala Pro Ser Lys Gln Leu Cys Met Asn Gly Thr Glu Ser
385                 390                 395                 400

Gln Leu Lys Thr Glu Arg Arg Val Ser Ser Ser Gln Arg Lys Ala
                405                 410                 415

Ser Thr Thr Gly Ser Lys Val Arg Lys Leu Ser Ala Cys Lys Gln Gln
                420                 425                 430

(2) INFORMATION FOR SEQ ID NO:7:

(i) SEQUENCE CHARACTERISTICS:
        (A) LENGTH: 525 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 189508

(xi) SEQUENCE DESCRIPTION: SEQ ID NO:7:

Met Arg Arg Arg Arg Arg Asp Gly Phe Tyr Pro Ala Pro Asp Phe
1               5                   10                  15

Arg Asp Arg Glu Ala Glu Asp Met Ala Gly Val Phe Asp Ile Asp Leu
                20                  25                  30

Asp Gln Pro Glu Asp Ala Gly Ser Glu Asp Glu Leu Glu Glu Gly Gly
            35                  40                  45

Gln Leu Asn Glu Ser Met Asp His Gly Gly Val Gly Pro Tyr Glu Leu
50                  55                  60

Gly Met Glu His Cys Glu Lys Phe Glu Ile Ser Glu Thr Ser Val Asn
65                  70                  75                  80

Arg Gly Pro Glu Lys Ile Arg Pro Glu Cys Phe Glu Leu Leu Arg Val
                85                  90                  95

Leu Gly Lys Gly Gly Tyr Gly Lys Val Phe Gln Val Arg Lys Val Thr
            100                 105                 110

Gly Ala Asn Thr Gly Lys Ile Phe Ala Met Lys Val Leu Lys Lys Ala
            115                 120                 125

Met Ile Val Arg Asn Ala Lys Asp Thr Ala His Thr Lys Ala Glu Arg
130                 135                 140

Asn Ile Leu Glu Glu Val Lys His Pro Phe Ile Val Asp Leu Ile Tyr
145                 150                 155                 160

Ala Phe Gln Thr Gly Gly Lys Leu Tyr Leu Ile Leu Glu Tyr Leu Ser
                165                 170                 175

Gly Gly Glu Leu Phe Met Gln Leu Glu Arg Glu Gly Ile Phe Met Glu
            180                 185                 190

Asp Thr Ala Cys Phe Tyr Leu Ala Glu Ile Ser Met Ala Leu Gly His
            195                 200                 205

Leu His Gln Lys Gly Ile Ile Tyr Arg Asp Leu Lys Pro Glu Asn Ile
        210                 215                 220

Met Leu Asn His Gln Gly His Val Lys Leu Thr Asp Phe Gly Leu Cys
225                 230                 235                 240

Lys Glu Ser Ile His Asp Gly Thr Val Thr His Thr Phe Cys Gly Thr
                245                 250                 255

Ile Glu Tyr Met Ala Pro Glu Ile Leu Met Arg Ser Gly His Asn Arg
            260                 265                 270
```

```
Ala Val Asp Trp Trp Ser Leu Gly Ala Leu Met Tyr Asp Met Leu Thr
        275                 280                 285

Gly Ala Pro Pro Phe Thr Gly Glu Asn Arg Lys Lys Thr Ile Asp Lys
        290                 295                 300

Ile Leu Lys Cys Lys Leu Asn Leu Pro Pro Tyr Leu Thr Gln Glu Ala
305                 310                 315                 320

Arg Asp Leu Leu Lys Lys Leu Leu Lys Arg Asn Ala Ala Ser Arg Leu
                325                 330                 335

Gly Ala Gly Pro Gly Asp Ala Gly Glu Val Gln Ala His Pro Phe Phe
                340                 345                 350

Arg His Ile Asn Trp Glu Glu Leu Leu Ala Arg Lys Val Glu Pro Pro
        355                 360                 365

Phe Lys Pro Leu Leu Gln Ser Glu Glu Asp Val Ser Gln Phe Asp Ser
        370                 375                 380

Lys Phe Thr Arg Gln Thr Pro Val Asp Ser Pro Asp Asp Ser Thr Leu
385                 390                 395                 400

Ser Glu Ser Ala Asn Gln Val Phe Leu Gly Phe Thr Tyr Val Ala Pro
                405                 410                 415

Ser Val Leu Glu Ser Val Lys Glu Lys Phe Ser Phe Glu Pro Lys Ile
                420                 425                 430

Arg Ser Pro Arg Arg Phe Ile Gly Ser Pro Arg Thr Pro Val Ser Pro
        435                 440                 445

Val Lys Phe Ser Pro Gly Asp Phe Trp Gly Arg Gly Ala Ser Ala Ser
        450                 455                 460

Thr Ala Asn Pro Gln Thr Pro Val Glu Tyr Pro Met Glu Thr Ser Gly
465                 470                 475                 480

Ile Glu Gln Met Asp Val Thr Met Ser Gly Glu Ala Ser Ala Pro Leu
                485                 490                 495

Pro Ile Arg Gln Pro Asn Ser Gly Pro Tyr Lys Lys Gln Ala Phe Pro
                500                 505                 510

Met Ile Ser Lys Arg Pro Glu His Leu Arg Met Asn Leu
                515                 520                 525

(2) INFORMATION FOR SEQ ID NO:8:

(i) SEQUENCE CHARACTERISTICS:
        (A) LENGTH: 525 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 1562

(xi) SEQUENCE DESCRIPTION: SEQ ID NO:8:

Met Arg Arg Arg Arg Arg Asp Gly Phe Tyr Pro Ala Pro Asp Phe
1               5                   10                  15

Arg Asp Arg Glu Ala Glu Asp Met Ala Gly Val Phe Asp Ile Asp Leu
                20                  25                  30

Asp Gln Pro Glu Asp Ala Gly Ser Glu Asp Glu Leu Glu Glu Gly Gly
            35                  40                  45

Gln Leu Asn Glu Ser Met Asp His Gly Gly Val Gly Pro Tyr Glu Leu
50                  55                  60

Gly Met Glu His Cys Glu Lys Phe Glu Ile Ser Glu Thr Ser Val Asn
65                  70                  75                  80
```

-continued

```
Arg Gly Pro Glu Lys Ile Arg Pro Glu Cys Phe Glu Leu Leu Arg Val
                85                  90                  95
Leu Gly Lys Gly Gly Tyr Gly Lys Val Phe Gln Val Arg Lys Val Thr
            100                 105                 110
Gly Ala Asn Thr Gly Lys Ile Phe Ala Met Lys Val Leu Lys Lys Ala
            115                 120                 125
Met Ile Val Arg Asn Ala Lys Asp Thr Ala His Thr Lys Ala Glu Arg
130                 135                 140
Asn Ile Leu Glu Glu Val Lys His Pro Phe Ile Val Asp Leu Ile Tyr
145                 150                 155                 160
Ala Phe Gln Thr Gly Gly Lys Leu Tyr Leu Ile Leu Glu Tyr Leu Ser
                165                 170                 175
Gly Gly Glu Leu Phe Met Gln Leu Glu Arg Glu Gly Ile Phe Met Glu
            180                 185                 190
Asp Thr Ala Cys Phe Tyr Leu Ala Glu Ile Ser Met Ala Leu Gly His
            195                 200                 205
Leu His Gln Lys Gly Ile Ile Tyr Arg Asp Leu Lys Pro Glu Asn Ile
210                 215                 220
Met Leu Asn His Gln Gly His Val Lys Leu Thr Asp Phe Gly Leu Cys
225                 230                 235                 240
Lys Glu Ser Ile His Asp Gly Thr Val Thr His Thr Phe Cys Gly Thr
                245                 250                 255
Ile Glu Tyr Met Ala Pro Glu Ile Leu Met Arg Ser Gly His Asn Arg
            260                 265                 270
Ala Val Asp Trp Trp Ser Leu Gly Ala Leu Met Tyr Asp Met Leu Thr
            275                 280                 285
Gly Ala Pro Pro Phe Thr Gly Glu Asn Arg Lys Lys Thr Ile Asp Lys
290                 295                 300
Ile Leu Lys Cys Lys Leu Asn Leu Pro Pro Tyr Leu Thr Gln Glu Ala
305                 310                 315                 320
Arg Asp Leu Leu Lys Lys Leu Leu Lys Arg Asn Ala Ala Ser Arg Leu
                325                 330                 335
Gly Ala Gly Pro Gly Asp Ala Gly Glu Val Gln Ala His Pro Phe Phe
            340                 345                 350
Arg His Ile Asn Trp Glu Glu Leu Leu Ala Arg Lys Val Glu Pro Pro
            355                 360                 365
Phe Lys Pro Leu Leu Gln Ser Glu Glu Asp Val Ser Gln Phe Asp Ser
370                 375                 380
Lys Phe Thr Arg Gln Thr Pro Val Asp Ser Pro Asp Asp Ser Thr Leu
385                 390                 395                 400
Ser Glu Ser Ala Asn Gln Val Phe Leu Gly Phe Thr Tyr Val Ala Pro
                405                 410                 415
Ser Val Leu Glu Ser Val Lys Glu Lys Phe Ser Phe Glu Pro Lys Ile
            420                 425                 430
Arg Ser Pro Arg Arg Phe Ile Gly Ser Pro Arg Thr Pro Val Ser Pro
            435                 440                 445
Val Lys Phe Ser Pro Gly Asp Phe Trp Gly Arg Gly Ala Ser Ala Ser
450                 455                 460
Thr Ala Asn Pro Gln Thr Pro Val Glu Tyr Pro Met Glu Thr Ser Gly
465                 470                 475                 480
Ile Glu Gln Met Asp Val Thr Thr Ser Gly Glu Ala Ser Ala Pro Leu
                485                 490                 495
```

```
Pro Ile Arg Gln Pro Asn Ser Gly Pro Tyr Lys Lys Gln Ala Phe Pro
            500                 505                 510

Met Ile Ser Lys Arg Pro Glu His Leu Arg Met Asn Leu
            515                 520                 525
```